United States Patent [19]
Sun et al.

[11] Patent Number: 5,788,814
[45] Date of Patent: Aug. 4, 1998

[54] CHUCKS AND METHODS FOR POSITIONING MULTIPLE OBJECTS ON A SUBSTRATE

[75] Inventors: Hoi Cheong Steve Sun, Plainsboro, N.J.; Christina Marie Knoedler, Newtown, Pa.

[73] Assignee: David Sarnoff Research Center, Princeton, N.J.

[21] Appl. No.: 630,012

[22] Filed: Apr. 9, 1996

[51] Int. Cl.$^6$ .......................... C25D 17/04; C25D 17/06; B23B 5/22; B23B 5/34
[52] U.S. Cl. ................... 204/297 R; 204/297 M; 279/3; 279/128; 118/DIG. 2
[58] Field of Search .......................... 204/297 R, 297 M, 204/198; 414/212, 332, 676; 269/21; 279/3, 128; 118/DIG. 2

[56] References Cited

U.S. PATENT DOCUMENTS

| | | | |
|---|---|---|---|
| 1,121,452 | 12/1914 | Bagnall | 279/3 |
| 4,160,257 | 7/1979 | Carrish | 346/159 |
| 4,332,789 | 6/1982 | Mlodozeniec | 424/27 |
| 4,561,688 | 12/1985 | Tsutsui | 279/3 |
| 4,652,318 | 3/1987 | Masuda et al. | 156/89 |
| 4,917,978 | 4/1990 | Ritt et al. | 430/23 |
| 4,921,727 | 5/1990 | Datta et al. | 427/57 |
| 4,921,767 | 5/1990 | Datta et al. | 430/23 |
| 4,925,701 | 5/1990 | Jansen et al. | 427/38 |
| 4,971,257 | 11/1990 | Birge | 239/708 |
| 5,028,501 | 7/1991 | Ritt et al. | 430/23 |
| 5,080,380 | 1/1992 | Nakagawa et al. | 279/128 |
| 5,278,588 | 1/1994 | Kubelik | 346/159 |
| 5,499,487 | 3/1996 | McGill | 53/473 |

FOREIGN PATENT DOCUMENTS 2-48145 (A)   2/1990   Japan .

OTHER PUBLICATIONS

Donald A. Seanor, Triboelectrification of Polymers in K.C. Frisch and A. Patsis, Electrical Properties of Polymers (Technomic Publications, Westport, CT) pp. 37–58, Date unavailable.

Toshiya Watanabe et al., Electrostatic Force and Absorption Current of Alumina Electrostatic Chuck, Jpn. J. Appl. Phys. vol. 31, pp. 2145–2150 (1992), month unavailable.

Larry D. Harsough, Electrostatic Wafer Holding, Solid State Technology, pp. 87–90 (Jan. 1993).

John Field, Electrostatic Wafer Clamping for Next-Generation Manufacturing, Solid State Technology, pp. 91–98 (Sep. 1994).

J.-F. Daviet et al., Electrostatic Clamping Applied to Semiconductor Plasma Processing, I. Theoretical Modeling, J. Electrochem. Soc., vol. 140, No. 11, pp. 3245–3256 (Nov. 1993).

(List continued on next page.)

*Primary Examiner*—Kathryn L. Gorgos
*Assistant Examiner*—Edna Wong
*Attorney, Agent, or Firm*—William J. Burke

[57] ABSTRACT

The present invention relates to chucks and methods for positioning multiple objects, optionally for transport onto a recipient substrate. Instead of using conventional clamps that employ mechanical force, the present invention is directed to the use of a non-mechanical force such as negative pressure in a vacuum chuck, or static electricity in an electrostatic chuck as the force applied to the objects held by the chuck. Further, the chuck has a layer for holding the objects which are optionally subsequently transferred to a recipient substrate, the layer having a configuration substantially corresponding to the configuration of the recipient substrate. In certain aspects, the present invention is directed to a chuck for positioning objects with an average width or diameter less than or equal to one millimeter, and a thickness preferably less than about 3 millimeters, such as beads used in the chemical industry. In another aspect, the invention is directed to methods which involve the use of chucks, including methods for attracting an object or multiple objects, methods for positioning objects, methods for transporting objects, preferably substantially simultaneously, and methods of chemical manufacturing using the chucks.

10 Claims, 13 Drawing Sheets

OTHER PUBLICATIONS

J.-F. Daviet et al., Electrostatic Clamping Applied to Semiconductor Plasma Processing, II. Experimental Results, J. Electrochem. Soc., vol. 140, No. 11, pp. 3256–3261 (Nov. 1993).

Peter Singer, Electrostatic Chucks in Wafer Processing, Semiconductor International, pp. 57–64 (Apr. 1995).

T. Watanabe et al., Electrostatic Charge Distribution in the Dielectric Layer of Alumina Electrostatic Chuck, Journal of Materials Science, vol. 29, pp. 3510–3616 (1994), Month unavailable.

Mamoru Nakasuji et al., Low Voltage and High Speed Operating Electrostatic Wafer Chuck Using Sputtered Tantalum Oxide Membrane, J. Vac. Sci. Technol. A 12(5) pp. 2834–2839 (Sep./Oct. 1994).

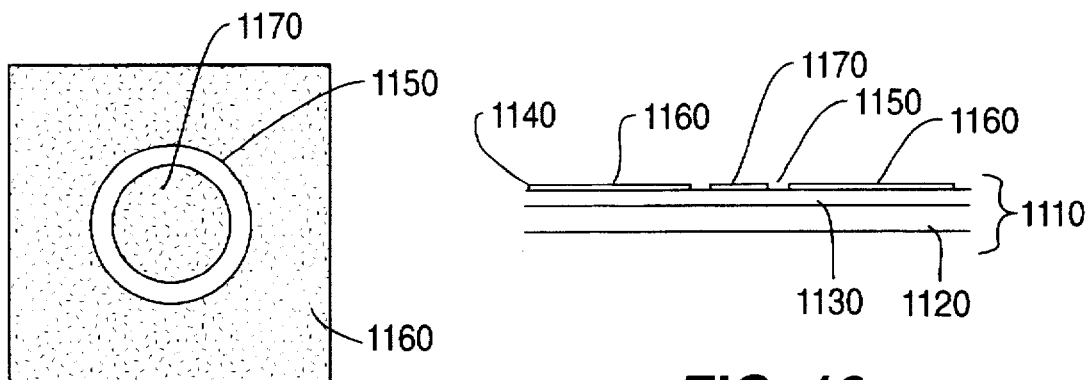
FIG. 11
FIG. 10
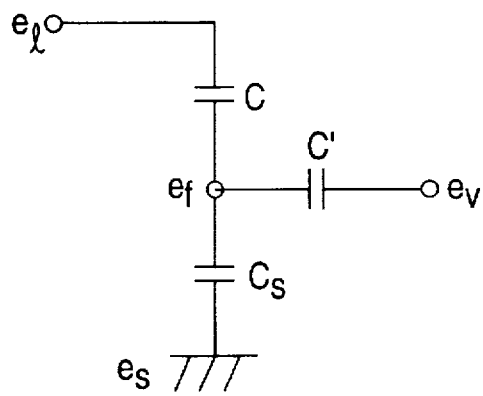
FIG. 12
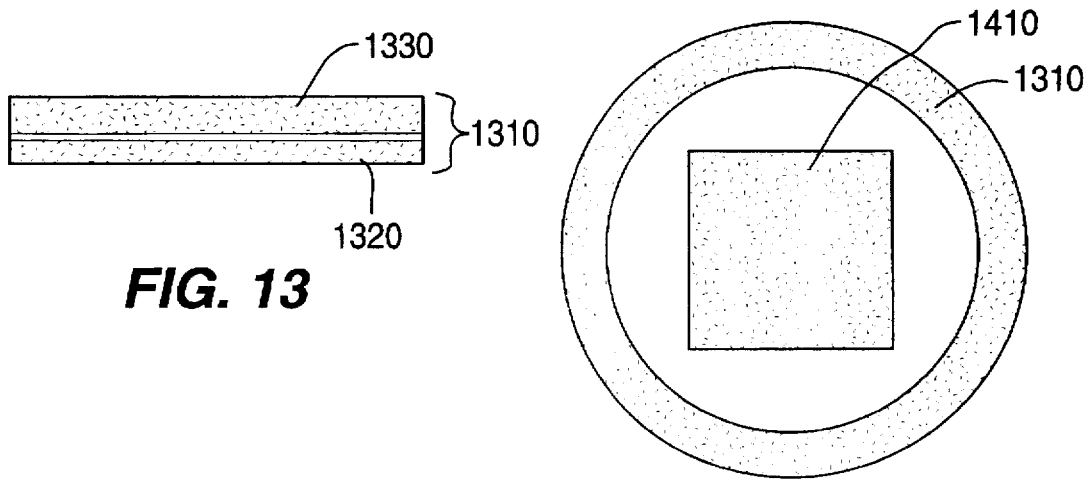
FIG. 13
FIG. 14

CHUCKS AND METHODS FOR POSITIONING MULTIPLE OBJECTS ON A SUBSTRATE

Synthetic beads, generally several hundred microns in diameter, are used in the chemical industry, for example, for support in chemical synthesis. For instance, such beads are used in combinatorial chemistry for solid-phase synthesis, which can result in thousands, and commonly tens of thousands, of different members of a combinatorial library. In combinatorial chemistry, a multi-well array such as a microtiter plate is used in order to screen a multiplicity of chemical compounds simultaneously. Each well requires the addition of an individual bead for such screening.

To add beads to an array having individual wells, the beads are added one at a time to the array, using, for example, a micropipette. The use of a micropipette to individually deposit beads on an array is inefficient, tedious and time-consuming, and commonly leads to clogging the opening of the micropipette. For example, assuming that it takes an average of about 30 seconds to place a single bead in each well, about 48 minutes would be required to set up the beads in a microtiter plate with 96 wells and more than 83 hours to set up the beads in a plate with 10,000 wells depositing multiple small objects, such as beads, on a substrate, including a multi-well microtiter plate. Therefore, there is a need for a more efficient means for positioning and

SUMMARY OF THE INVENTION

The disadvantages heretofore associated with the prior art are overcome by inventive technique and apparatus for simultaneously attracting multiple objects to a substrate. The present invention provides advantages including cost-effectiveness, efficiency, and, for example, the ability to simultaneously place individual beads in multiple wells.

The invention is directed to chucks and methods for positioning multiple objects, optionally for transport onto a recipient substrate. Chucks are defined herein as clamps for holding an object or objects. The objects can be released by the chuck when desired, such as when the objects are positioned for deposit onto the recipient substrate. Instead of using conventional mechanical clamps that are based on or employ compression, the present invention is directed to the use of negative pressure in a vacuum chuck, or static electricity in an electrostatic chuck, in order to hold as the force applied to the objects held by the chuck.

In one aspect, the present invention is directed to an apparatus for positioning multiple objects, such as beads, in a selected configuration, each object preferably having a thickness less than about 3 millimeters and an average width or diameter of less than or equal to about one millimeter, comprising: a non-mechanical chuck having a layer for holding the objects, the layer having a configuration substantially corresponding to the selected configuration. In preferred embodiments, the chuck is vacuum-based or electrostatic-based.

In another aspect, the invention is directed to an apparatus for transporting multiple objects, such as beads, to a recipient substrate having a configuration for receiving the objects, each object preferably having a thickness less than about 3 millimeters and an average width or diameter of less than or equal to about one millimeter, comprising: a non-mechanical chuck having a layer for holding the objects, the layer having a configuration substantially corresponding to the configuration of the recipient substrate. In preferred embodiments, the chuck is vacuum-based or electrostatic-based.

In addition to chucks, the present invention is also directed to methods which involve the use of chucks. For example, the present invention is directed to a method for positioning multiple objects, preferably having a thickness less than about 3 millimeters and a diameter less than about one millimeter, such as beads, in a selected configuration comprising:

(a) providing a non-mechanical chuck having a layer for holding the objects, the layer having a configuration substantially corresponding to the selected configuration;

(b) applying the objects to the chuck; and (c) positioning the objects using the chuck. Preferably, the methods involve the use of chucks that are vacuum-based or electrostatic-based.

In a further aspect, the present invention is directed to a method for transporting multiple objects, such as beads, to a recipient substrate having a configuration for receiving the objects, each object preferably having an average diameter less than about one millimeter, comprising:

(a) providing a non-mechanical chuck, such as a vacuum chuck or an electrostatic chuck, having a layer for holding the objects, the layer having a configuration substantially corresponding to the configuration of the recipient substrate;

(b) applying the objects to the chuck; and (c) transporting the objects to the recipient substrate. Preferably, this method involves the use of a chuck that is vacuum-based or electrostatic-based. This method preferably includes aligning the chuck and the recipient substrate before transporting the objects, and releasing the objects by releasing or reversing the effect of the non-mechanical chuck, which works by vacuum or electrostatic means, for example.

The chucks of the present invention attract the objects through the use of non-mechanical force, such as electrostatic force or negative pressure, in the electrostatic chuck and the vacuum chuck, respectively.

In another aspect, the present invention is directed to a vacuum chuck for attracting multiple objects, preferably substantially simultaneously, the chuck comprising:

(a) a substrate having multiple open vias, each via permitting air flow;

(b) a bottom layer attached to the substrate;

(c) a cavity between the bottom layer and the substrate, the cavity permitting air flow between the bottom layer and the substrate; and (d) a pathway, such as an opening, for connecting the bottom layer to a vacuum source, wherein each via extends through the substrate to the cavity such that each via is subjected to negative pressure when a vacuum source is applied to the pathway. In preferred embodiments, the diameter of the vias is smaller than the diameter of the objects, and in certain embodiments, the diameter of the vias is about 50 microns to about 75 microns.

The vacuum chuck of the invention can be used with numerous types of objects, including beads, which can include more than one type of bead, and which preferably have a diameter greater than about 100 microns, and more preferably, have a diameter from about 100 to about 300 microns, and most preferably, have a diameter of from about 125 to about 175 microns, such as 150 microns. The beads are preferably comprised of a polymer, for example, such as one selected from the group consisting of divinylbenzene copolymer, polystyrene, and polyethylene glycol. The bead can either be substantially dry or have substantially absorbed an aqueous solution.

The non-mechanical chucks of the invention, such as vacuum and electrostatic chucks, are used, for example, in a method for transporting beads to an array having multiple wells, such as a microtiter plate, wherein the chuck has a corresponding via for each well of the array. The method comprises (a) providing a non-mechanical chuck for holding the beads in a configuration substantially corresponding to the array, such as the wells of the microtiter plate; (b) applying the beads to the chuck; and (c) transporting the beads to the array, such as the wells of the microtiter plate. The method further comprises aligning the chuck to the microtiter plate, wherein about one bead is deposited into each well of the plate. Each well of the array has a pitch, which is defined as the distance of one edge of a well to the corresponding edge of the adjacent well. In preferred embodiments, each via of the chuck has a pitch that is substantially the same as the pitch of the corresponding well in the array.

The present invention also relates to a vacuum chuck for substantially simultaneously attracting multiple objects, such as beads, preferably including more than one type of bead, comprising:

(a) a substrate having multiple open vias, each via permitting air flow;
(b) a bottom layer attached to the substrate;
(c) a cavity between the bottom layer and the substrate, the cavity permitting air flow between the bottom layer and the substrate; and
(d) a pathway for connecting the bottom layer to a vacuum source, wherein each via extends through the substrate to the cavity such that each via is subjected to negative pressure when a vacuum source is applied to the pathway.

The vacuum chuck can be made of a number of materials, and in certain embodiments, the solid substrate of the vacuum chuck is made of glass, which preferably has a thickness of about 10 to about 20 mils, and preferably includes a configuration of vias having a selected number of rows and columns, for example, that correspond to the recipient substrate, which is preferably a microtiter plate. Preferably, the vias are laser drilled and have diameters that are smaller than the diameters of the objects. In certain embodiments, the substrate has a row of about ten vias by a column of about ten vias; in other embodiments, the substrate has a row of about 100 vias by a column of about 100 vias. In certain aspects of the invention, the total number of vias on the substrate is about 96 to about 100, and in other aspects, the total number of vias is about 10,000. The beads used in the context of the vacuum chuck have a diameter of from above 100 to above 300 microns, and preferably comprise a polymer, wherein the polymer is selected from the group consisting of divinylbenzene copolymer, polystyrene, and polyethylene glycol. Such beads are preferably substantially dry or have substantially absorbed an aqueous solution.

The present invention is also directed to methods for simultaneously adhering multiple objects onto a vacuum chuck by: (a) applying a vacuum to the chuck; and (b) applying the objects to the chuck, wherein the objects adhere to the chuck through a vacuum. This method can further include (c) transporting the objects to a recipient substrate by inverting the chuck over the recipient substrate and releasing the vacuum, and the process can be repeated whereby the chuck is used more than once. The methods of the invention can be used with numerous and various objects, including beads, and the methods can be used to deposit objects such as beads onto a recipient substrate which is an array of multiple wells, such as a microtiter plate. Preferably, the methods of the invention provide for about one bead to be released into each well of the array.

In addition to vacuum chucks, the present invention is also directed to the use of electrostatic attraction to adhere multiple objects to a chuck. Thus, in another aspect, the invention is directed to a chuck for electrostatically attracting multiple objects, such as beads, the chuck comprising:

(a) a substrate having a top and a bottom;
(b) vias extending from the top to the bottom of the substrate, the vias comprising a conductive material;
(c) a dielectric layer on the top and the bottom of the substrate; and
(d) a conductive layer contacting at least one of the dielectric layers. This chuck is referred to herein as an "electrostatic chuck with conductive vias". In preferred embodiments of this electrostatic chuck, the conductive material in the vias does not extend beyond the surface of the substrate. Preferably, the conductive material in the vias comprises a conductive ink. The conductive layer on one of the dielectric layers preferably comprises a metal, such as indium tin oxide, brass, or copper, and is preferably about 500 nm in thickness. The conductive layer is attached to a power source during use of the electrostatic chuck.

In another preferred aspect, the present invention is directed to an electrostatic chuck for electrostatically attracting multiple objects, such as beads, the chuck comprising:

(a) a lower conductive layer;
(b) a middle dielectric layer; and
(c) an upper conductive layer, the upper conductive layer having openings exposing the middle dielectric layer. Preferably, the diameter of the openings in the upper conductive layer is smaller than the diameter of the objects. The openings in the upper conductive layer of the chuck preferably have a configuration that corresponds to the configuration of the wells in a microtiter plate. Further, in preferred embodiments, the dielectric material forming the middle layer is rated to withstand at least about 500 volts, and preferably 3000 volts.

Additionally, the present invention is directed to methods for electrostatically attracting multiple objects, such as beads, comprising: (a) providing an electrostatic chuck; (b) applying a voltage source to the chuck; and (c) applying electrostatically charged objects to the chuck, thereby attracting the objects to the chuck. In certain embodiments, step (b) of the method for electrostatically attracting multiple objects comprises:

(i) applying a voltage having a polarity to a first metal layer of the chuck, the first metal layer being on top of vias extending through a layer of the chuck; and
(ii) applying a voltage of opposite polarity to a second metal layer of the chuck, wherein the second metal layer is positioned below the vias, preferably thereby inducing a charge of one polarity on the bottom of the vias and a charge of the opposite polarity on the top of the vias, whereby the polarity of the top of the via is opposite in polarity to the charge of most of the beads to be attracted to the chuck. In other embodiments, using the preferred electrostatic chuck described above, step (b) comprises applying a selected voltage to a lower conductive layer of the chuck. Preferably, the objects are electrostatically charged before applying them to the chuck.

Further, the present invention is directed to a method of chemical manufacturing comprising using an electrostatic chuck to attract multiple objects, such as beads, to a substrate, wherein the objects support a chemical reaction. Additionally, the present invention provides the use of the electrostatic chuck to attract multiple objects. This use is preferably effected wherein multiple objects, such as multiple beads are used to support a chemical reaction for a chemical assay or chemical manufacturing. For example, the electrostatic chuck can be used to attract multiple beads to a substrate, and to hold beads on a substrate against gravitational forces. The chuck can also be used to substantially simultaneously position multiple beads. The chuck can then be used to substantially simultaneously transport the beads to a recipient substrate, such as a substrate having multiple wells, wherein the use of the chuck further comprises transporting about one bead to each well. Furthermore, the invention provides for the use of an electrostatic chuck having a bias potential for attracting a bead to a substrate, preferably wherein the bias potential is greater than about 200 volts, more preferably greater than about 1000 volts.

BRIEF DESCRIPTION OF THE DRAWINGS

FIG. 10 is a cross-sectional schematic view of an electrostatic chuck with floating electrodes on the upper conductive layer for charge imaging.

FIG. 11 is a top view of a floating electrode of FIG. 10.

FIG. 12 is a circuit diagram of an electrostatic chuck with a floating electrode on the upper conductive layer.

FIG. 13 is a schematic cross-sectional view of a sensing electrode.

FIG. 14 is a top schematic view of a sensing electrode, with the location of the sensing electrode being outside the area of deposition.

FIG. 27A shows the electrostatic chuck circuit; FIG. 27B shows a window mask for the chuck and FIG. 27C shows the chuck assembly with an array of tablets.

DETAILED DESCRIPTION OF THE INVENTION

Figure 1:
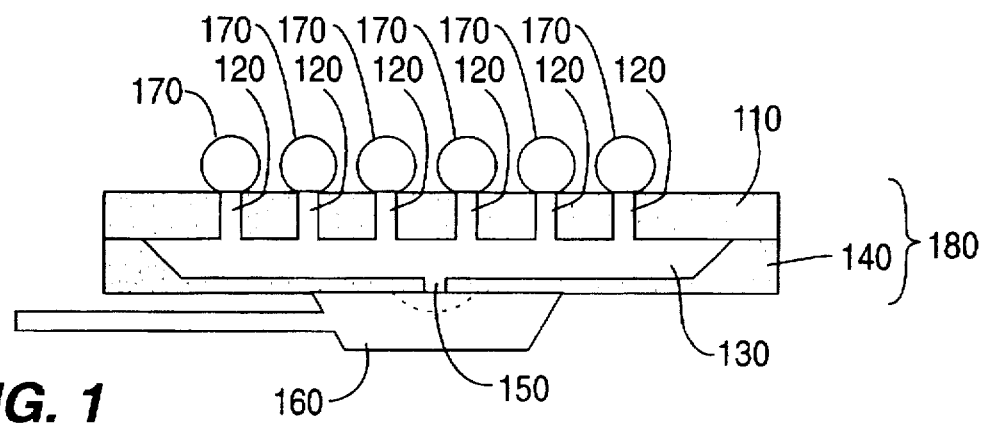
FIG. 1 is a cross-sectional view of a schematic representation of a vacuum chuck for positioning objects according to the present invention.

This application has been filed simultaneously with co-pending applications entitled "Plate static Chucks", "Acoustic Dispenser" and "Plate for Reaction Systems", which are hereby incorporated herein by reference, in their entirety.

For purposes of this application, the following terms have the indicated meanings.

Acoustic dispenser: an apparatus for dispensing particles that employs vibration having a frequency in the acoustic (audible) range.

Chuck: a clamp for holding an object or objects.

Chuck for positioning objects: a chuck having a configuration that can be used for substantially arranging objects on the chuck in a selected pattern.

Electrostatic chuck: a clamp for holding an object or objects using electrostatic force.

Electrostatic chuck with conductive vias: an electrostatic chuck for positioning objects, in which the chuck has a layer that determines the positioning of the objects, and this layer has vias containing a conductive material.

Mechanical Chuck: a chuck that uses compression to hold an object.

Non-Mechanical Chuck: a chuck that does not use compression to hold an object, including but not limited to a chuck that uses electrostatic or vacuum (i.e., negative pressure) means for such holding.

Object: a material thing.

Particle: an object equal to or less than about one millimeter in width or diameter.

Pitch: the repeat distance between the edge of one well to the corresponding edge of the adjacent well in, for example, a microtiter plate.

Recipient substrate: a substrate for receiving objects released from a chuck.

Substrate: a surface or layer.

Upper conductive layer: the conductive layer of an electrostatic chuck that attracts or adheres objects to the chuck.

Vacuum chuck: a clamp for holding an object or objects using negative pressure.

Via: a passageway.

The invention is directed, in part, to chucks and methods for positioning multiple objects, and optionally for transport of such objects onto a recipient substrate. "Chucks" are defined above as clamps for holding an object or objects. Instead of using conventional clamps that employ mechanical or compressive force, the present invention is directed to the use of negative pressure in a vacuum chuck, or static electricity in an electrostatic chuck as the means used by the context of the chuck to hold objects. The objects can optionally be positioned, transported and deposited. Preferably, the chucks use a force other than positive pressure for holding objects.

In one aspect, the present invention is directed to a "chuck for positioning objects," which is defined as a chuck having a configuration for arranging objects on the chuck in a selected pattern. Chucks for positioning objects can be used to transport multiple objects, such as beads, in a selected configuration onto a recipient substrate. Each object preferably has an average width or diameter less than or equal to about one millimeter, and each object preferably has a thickness less than about 3 millimeters.

The chuck for positioning objects in a selected configuration comprises: a chuck having a layer for holding the objects, the layer having a configuration that substantially corresponds to the selected configuration, wherein the chuck is a non-mechanical chuck, such as a vacuum chuck or an electrostatic chuck. Where the chuck for positioning objects is used for transporting the objects to a recipient substrate, the configuration of the layer of the chuck substantially corresponds to the configuration of the recipient substrate.

In addition to chucks, the present invention is also directed to methods which involve the use of chucks. For example, the present invention is directed to a method for positioning, and optionally transporting, multiple objects, preferably having a diameter less than about one millimeter, and preferably having a thickness less than about 3 millimeters, such as beads, in a selected configuration. These methods comprise:

(a) providing a chuck having a layer for holding the objects, the layer having a configuration substantially corresponding to the selected configuration; and (b) applying the objects to the chuck, such as a vacuum chuck or an electrostatic chuck, wherein the objects adhere to the chuck through a non-mechanical, non-compressive force. In methods for transporting objects, the configuration of the layer of the chuck substantially corresponds to the configuration of the recipient substrate and the method further includes (c) transporting the objects to the recipient substrate. This method preferably includes aligning the chuck and the recipient substrate before transporting the objects, and releasing the objects by releasing or reversing the non-mechanical force.

In one aspect of the invention, a vacuum or an electrostatic chuck is the chuck used for positioning objects which can be used in a chemical assay or to manufacture chemicals or pharmaceuticals. In certain preferred embodiments, the object is a bead, and the design of the chuck is used to position the beads on the chuck and subsequently transfer the beads onto the corresponding positions of a multi-well array, such as a microtiter plate, including the microtiter plates described in the application entitled "Plate for Reaction Systems." When the objects are transported to a recipient substrate having an array of multiple wells, preferably about one object is released into each well of the array.

Thus, in certain embodiments, the present invention provides for the use of a chuck to position and optionally transfer multiple objects. In preferred embodiments, the objects are spherical, and preferably, the objects are beads, which can be used to support chemical synthesis, for example, in combinatorial chemistry or in an assay, using, for example, PCR (polymerase chain reaction).

The chucks for positioning objects can also be used, for example, to transfer objects such as beads from one part of an array to another part of the same array. For example, the wells of a single array can be divided such that half of the array is used for synthesis. After synthesis, the beads are transferred to the other half of the array, which is used, for example, for an assay or multiple assays. Alternatively, for example, the chucks for positioning objects can be used to transfer objects such as beads from one array to a separate array.

In preferred embodiments, a vacuum chuck for positioning objects contains (a) a substrate having multiple open vias, each via permitting air flow; (b) a bottom layer attached to the substrate; (c) a cavity between the bottom layer and the substrate, the cavity permitting air flow between the bottom layer and the substrate; and (d) a pathway for connecting the bottom layer to a vacuum source, wherein each via extends through the substrate to the cavity such that each via is subjected to negative pressure when a vacuum source is applied to the pathway. The bottom layer has a pathway, such as an opening, for the application of negative pressure from a vacuum source through the cavity to the vias, which attracts objects by negative pressure.

The term "via", as used herein, is defined as a passageway, and the passageway preferably extends from the top surface of the substrate to the bottom surface of the substrate.

Referring to FIG. 1, for example, the upper layer of the substrate 110 has multiple open vias 120 which are connected to a cavity 130 in the bottom layer 140. The bottom layer of the substrate has an opening 150 for connecting the bottom layer to a vacuum source 160. The beads 170 are held by the chuck 180 using negative pressure applied through the vacuum source 160.

The objects can be applied to an electrostatic or vacuum chuck for positioning objects by, for example, pouring them onto the top of the chuck. Alternatively, for example, the objects can be applied using an acoustic dispenser described below. Excess objects are preferably removed once about one object is attached to each via. When using the vacuum chuck, the negative pressure is turned off to release the objects. Alternatively, for example, positive pressure is applied to repel the objects from the vacuum chuck. The objects can be released into a substrate such as a microtiter plate, for example, after lining up the vias of the chuck to correspond to the wells in the plate.

Preferably, the diameter of the vias in the vacuum chuck for positioning objects is smaller than the diameter of the objects to be held by the chuck. In preferred embodiments in which the chuck is used to hold a bead having an average diameter of about 150 microns, the diameter of the vias is about 50 microns to about 75 microns.

When a chuck for positioning objects is used to transport multiple objects to an array having multiple wells, the chuck preferably has a corresponding via for each well of the array. Additionally, in preferred embodiments, each via of the chuck has a pitch that is substantially the same as the pitch of the corresponding well in the array. The "pitch" is defined above as the repeat distance between the edge of one well to the corresponding edge of the adjacent well. Thus, the configuration of the chuck which matches the configuration of the recipient array causes the beads to align so that there will generally be one bead per well when the beads are transferred to the array. Hence, the chucks of the present invention can be used to position objects, and optionally, subsequently transfer the objects onto a recipient substrate. Preferably, the chuck and the recipient substrate are marked for alignment, such as mechanically or optically. See, for example, the application entitled "Plate for Reaction Systems".

By way of example, when used to attract multiple objects for transport onto an array such as a microtiter plate having 100 wells in a row of ten wells by a column of ten wells, preferably the substrate of the chuck includes an array of vias or openings having a row of ten vias by a column of ten vias. In other embodiments, the microtiter plate has 10,000 wells and the array of vias in the chuck has a row of about 100 vias by a column of about 100 vias. In certain preferred embodiments, the total number of vias on the substrate of the chuck is about 96, to correspond to a 96 well microtiter plate.

In certain preferred embodiments, the vias are laser drilled, using, for example, an excimer laser. The vias can be drilled, for example, using a mask to establish the pattern for laser etching. Alternatively, for example, the holes can be drilled using a mandril with a mold to determine the placement of the vias.

The chucks of the present invention can be used to attract more than one type of object. In certain embodiments, the chuck is used with beads having a diameter greater than about 100 microns, and more preferably, a diameter from about 100 to about 500 microns, and in certain embodiments, a diameter of about 150 microns. The beads can be made of a polymer, such as a divinylbenzene copolymer, polystyrene or polyethylene glycol. The beads can either be dry or wet, having absorbed an aqueous solution. Examples of suppliers of beads include PerSeptive Biosystems' (Framingham, Mass.) PEG-PS, which is a polyethylene glycol graft polystyrene and Rapp Polymer GmbH's TentaGel, which is a cross-linked polyethylene glycol resin.

In preferred embodiments, the materials used to form the vacuum chucks for positioning objects are as follows. The vacuum chuck, and in certain embodiments, the electrostatic chuck for positioning objects, preferably has a substrate made of glass, and in preferred embodiments, the glass has a thickness of about 10 to about 20 mils. For example, Corning Pyrex 7740 glass (Corning Inc, Corning, N.Y.) can be used.

The vacuum wand for use with the vacuum chuck of the present invention is preferably a pencil-like barrel with an interior channel connected to a vacuum source. There is a small vacuum orifice which, when covered by a finger, transfers the vacuum to the tip or paddle of the wand. There is a secondary bleed hole near the tip to assure release when the vacuum orifice is uncovered. The vacuum wand can be obtained, for example, from H-Square Corp. (Sunnyvale, Calif.).

In one aspect, the present invention is directed to methods for simultaneously adhering multiple objects onto a vacuum chuck. These methods include (a) providing a vacuum chuck; (b) applying a vacuum to the chuck; and (c) applying the objects to the chuck, wherein the objects adhere to the chuck through the negative pressure of the vacuum. In preferred embodiments, the method further includes (d) transporting the objects to a recipient substrate by inverting the chuck over the recipient substrate and releasing the vacuum. The chucks of the present invention are preferably reusable; therefore, in preferred embodiments, the process is repeated whereby the chuck is used more than once.

In addition to vacuum chucks, the present invention also provides electrostatic chucks for electrostatically attracting an object or multiple objects. Without being limited to any particular theory, it is believed that when an electric potential is applied to the electrostatic chucks of the invention, capacitors are formed between the electrodes of the chuck and objects are held by the electrostatic force. One of the advantages of using an electrostatic chuck in the chemical or pharmaceutical industry is that, unlike plasma charging, electrostatic charging (also known as tribocharging) generally does not negatively affect chemicals. Further, the use of an electrostatic chuck provides the ability to hold a pharmaceutical substrate, for example, without requiring mechanical force that could disrupt the substrate.

When using an electrostatic chuck, preferably the temperature is between about −50° C. to about 200° C., and preferably from about 22° C. to about 60° C. The humidity is preferably between 0–100% wherein the humidity does not cause condensation; more preferably, the humidity is about 30%.

The present invention provides electrostatic chucks to hold a small object, such as a particle equal to or less than about one millimeter, and optionally, multiple small objects, preferably having a size from about 5 microns to about 500 microns, and preferably for use in the chemical or pharmaceutical industry. The use of an electrostatic chuck in the chemical and pharmaceutical industries is one of the novelties of the present invention.

In one aspect, the present invention provides for the use of an electrostatic chuck having a bias potential for attracting an object or objects to a substrate. Preferably, the bias potential is greater than about 1000 volts. The use of the chuck according to the present invention provides for the possibility of a bias potential since a bias potential does not necessarily cause damage to, for example, a pharmaceutical substrate, unlike a wafer in the semiconductor industry, which is voltage sensitive.

In certain embodiments, the electrostatic chuck for positioning objects comprises a dielectric substrate having conductive vias in it (an "electrostatic chuck with conductive vias"). Preferably, the chuck with co chuck with conductive vias has (a) a substrate having a top and a bottom; (b) vias extending from the top to the bottom of substrate, the vias comprising a conductive material; (c) a dielectric layer on each of the top and the bottom of the substrate; and (d) a conductive layer on the outside of one of the dielectric layers.

In preferred embodiments, the electrostatic chuck with conductive vias has two dielectric layers composed of a dielectric material that is rated to withstand about 2000 volts, which are each preferably less than about 50 microns in thickness. In the center of these two dielectric layers is a thicker dielectric substrate which can be made of glass, for example. In preferred embodiments, the dielectric substrate has good mechanical strength as well as high dielectric strength. Examples of dielectric materials that can be used include, but are not limited to ceramics, silicon dioxide, alumina, polyimide, aluminum oxide, titanium oxide, and titanates of calcium and magnesium. One type of glass that can be used for the dielectric substrate with the vias is Pyrex 7740 glass, and preferably the glass has a thickness of about 10 to about 20 mils.

In preferred embodiments of the electrostatic chuck with conductive vias, the dielectric substrate has via holes drilled through it which preferably do not extend into the dielectric layers on either side of the substrate. The via holes are preferably filled with conductive material. In preferred embodiments, the conductive material in the vias does not extend beyond the surface of the substrate, thus making the conductive material flush with the surface. In preferred embodiments, the conductive material in the vias comprises a conductive material such as a metal, for example a spherical gold powder, suspended in a carrier, such as a liquid suspension of resins, solvents and glass, thereby forming a conductive ink. The conductive ink is preferably dried and fired after filling the vias, thereby leaving a solid plug of conductive material in each via.

Preferably, the diameter of the vias is smaller than the diameter of the objects to be applied, such as the beads. Without being limited to a particular theory, it is believed that the use of a smaller diameter results in substantially avoiding the attraction of a second bead to the same via. Preferably, the vias are far enough apart from each other so that the attraction of an object to one via does not interfere with the attraction of an object to the adjacent via. More preferably, the distance between the vias is about twice the diameter of the bead.

Preferably, there is a lower conductive layer on the bottom of the electrostatic chuck with conductive vias, on the outside of one of the two dielectric layers. The conductive material can be layered onto the dielectric material, using for example, a standard process such as thin film coating or vacuum coating. Preferably, the conductive layer on the dielectric is about 1000 Angstroms to about 10 microns in thickness. In preferred embodiments, this conductive layer comprises a metal, and preferably is indium tin oxide, brass or copper.

Figure 2:
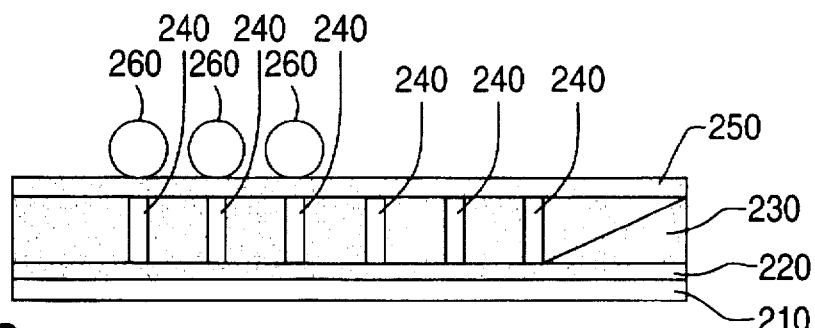
FIG. 2 is a cross-sectional view of a schematic representation of an electrostatic chuck with conductive vias according to the present invention.

Referring to FIG. 2, for example, there is a lower conductive layer 210 in the electrostatic chuck with conductive vias. On top of this layer is a dielectric layer 220. On top of the dielectric layer is a dielectric substrate 230 having via holes 240 extending through the substrate. The via holes 240 are filled with conductive ink. On top of the substrate is a second dielectric layer 250. Beads 260 are attracted to the positions corresponding to the vias, and are held in contact with the dielectric layer.

Other aspects of preferred embodiments of an electrostatic chuck include an insulating holder in contact with the conductive layer, the insulating holder having an electrical contact, such as a metal, attached to a power source. Alternatively, for example, the conductive layer can be charged by plasma charging. During the operation of the electrostatic chuck, a selected voltage is applied to the conductive layer. Preferably, the voltage applied is opposite in polarity to the charge on the objects to be applied to the chuck. Without being limited to a particular theory, it is believed that the application of voltage induces a surface charge on the conductive layer on one side of the conductive via. On the other side of the via, a charge is induced with equal but opposite polarity. The thickness of the substrate and thereby the length of the vias is believed to induce the separation of charge on one side of the via from the charge on the other side of the via. The electrostatically charged object is attracted to the top of the via, but the charge is not dissipated due to the presence of the dielectric layer between the via and the object. Further, since the diameter of the vias is smaller than the diameter of the objects, the charge of each via is shielded once an object is attracted to the via and a second object is less likely to be attracted to the via, thus resulting in one object per via.

Figure 3:
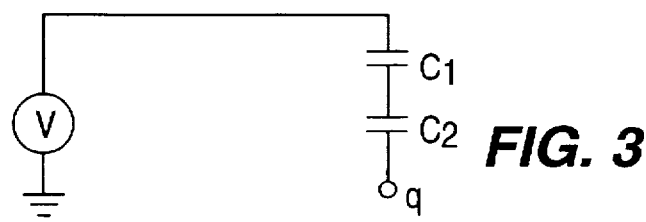
FIG. 3 is a circuit diagram of an electrostatic chuck with conductive vias according to the present invention.

A circuit diagram of an electrostatic chuck with conductive vias is provided in FIG. 3, in which $C_1$ is a capacitor formed between the lower conductive layer and a conductive via, $C_2$ is a capacitor formed between a conductive via and a charged object, such as a bead, and q is the charge from the charged object.

In preferred embodiments, the electrostatic chuck for positioning objects has an even simpler design than the electrostatic chuck with conductive vias. For example, an electrostatic chuck for positioning objects can have a dielectric layer between an upper conductive layer and a lower conductive layer, wherein each conductive layer functions as an electrode.

The upper conductive layer has openings in it which expose the dielectric layer below. The openings are preferably smaller than the objects to be attracted to the chuck. Like the electrostatic chuck with conductive vias, the openings are preferably arranged in the same spatial configuration as the recipient substrate, such as wells in a microtiter plate, onto which the objects will be transported. Preferably, the openings are made mechanically, such as through the use of a piercing object, for example, a laser drill. The openings can be spatially determined, for example, through the use of a mask with a positive photo resist.

Figure 4:
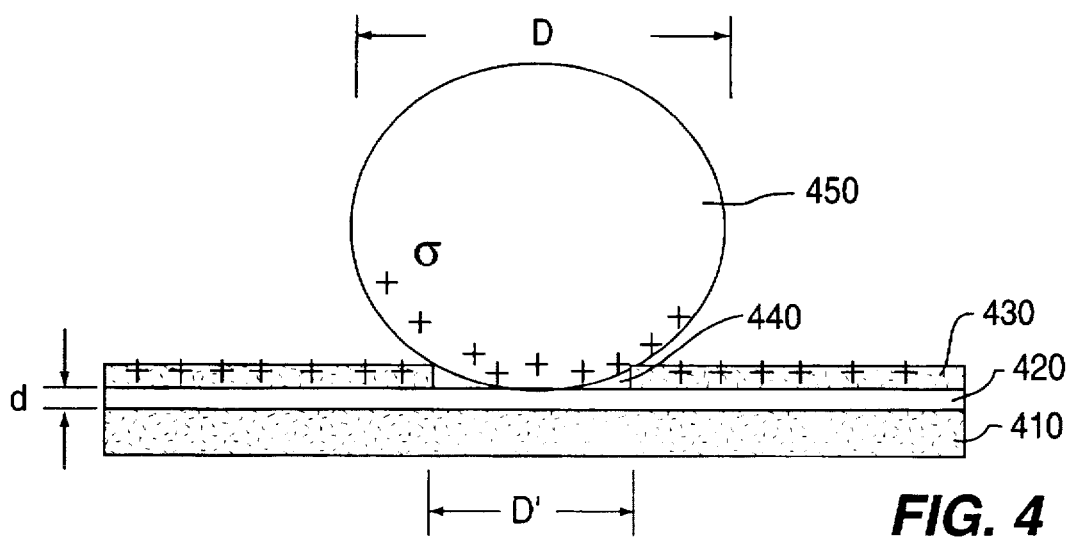
FIG. 4 is a cross-sectional view of a schematic representation of an electrostatic chuck with openings in the upper electrode for positioning objects according to the present invention.

Referring to FIG. 4, for example, the electrostatic chuck for positioning objects has a lower conductive layer 410, with a dielectric layer 420 on top of it. The dielectric layer 420 has a thin conductive layer 430 on top of it, and this conductive layer has openings 440 in it. The beads 450 are attracted to the openings in the upper conductive layer when voltage is applied to the lower conductive layer 410. The beads 450 can then be transported to a microtiter plate, for example, (not shown) and the beads 450 are released when the lower conductive layer 410 is shorted out or an opposite current is applied to the lower conductive layer 410 to repel the beads 450.

Figure 5:
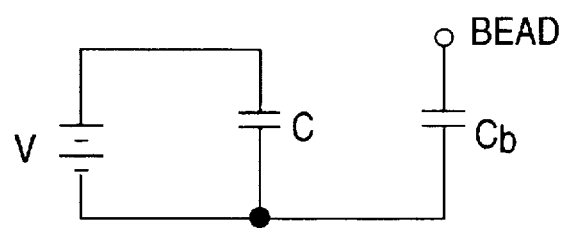
FIG. 5 is a circuit diagram of an electrostatic chuck, as shown in FIG. 4.

FIG. 5 illustrates a circuit diagram of the electrostatic chuck shown in FIG. 4. C is the capacitor formed between the upper and lower conductive layers. $C_b$ is the capacitor formed between the bead and the lower conductive layer.

Preferably, the lower conductive layer of the electrostatic chuck illustrated in FIG. 4 and described above has a thickness of about 10 microns. Preferably, the dielectric layer has a thickness of about 10 to about 100 microns, more preferably, less than about 50 microns. Preferably, the upper conductive layer is less than about 0.5 microns thick. More preferably, it is about 0.05 microns to about 0.5 microns. Preferably, for example, the openings in the upper conductive layer have a diameter about one-third of the size of the diameter of the objects to be attracted to the openings. For example, an electrostatic chuck designed to attract 300 micron beads preferably has openings having a diameter of about 100 microns.

In preferred embodiments, the dielectric layer is made of a material having good mechanical properties as well as high dielectric strength, such as silicon dioxide, alumina and polyimide. Preferably, the conductive layers are made of a good conductor, such as a metal, for example, indium tin oxide, brass and preferably silver.

Like the electrostatic chuck with conductive vias, the openings in the upper conductive layer of the above described chuck are preferably smaller than the diameter of the objects to be held by the chuck. Thus, since the diameter of the openings is smaller than the diameter of the objects, the charge of each opening is shielded once an object is attracted to the opening and a second object is less likely to be attracted to the opening, thus resulting in about one object per opening.

Without being limited to a particular theory, the following mathematical formulas can be used to approximate the holding force of the electrostatic chuck shown, for example, in FIG. 4.

If a bead lands on an opening or via of the electrostatic chuck, assuming that the bead carries a positive charge q, the capacitance $C_c$ of the electrostatic chuck can be approximated as the capacitance of a parallel plate capacitor and is given by:

$$C_c = \frac{\epsilon_0 \epsilon_r A}{d} \quad (1)$$

where d is the thickness of the dielectric layer, $\epsilon_r$ is the relative dielectric strength or dielectric constant of the dielectric layer, $\epsilon_o$ is the dielectric constant of a vacuum and A is the surface area of the top of the electrostatic chuck. Therefore, the capacitance density (per unit area) is:

$$\frac{C_c}{A} = \frac{\epsilon_0 \epsilon_r}{d} \quad (2)$$

since Q=CV for a capacitor where V is the potential across the capacitor and Q is the charge of the electrostatic chuck corresponding to the area below the opening. The charge density is Q/A and is related to $C_c$ by the following equation:

$$\frac{Q}{A} = \frac{C_c V}{A} = \frac{\epsilon_0 \epsilon_r V}{d} \quad (3)$$

It can be assumed that the charges of the bead are concentrated in one area or distributed throughout the bead. In reality, the situation is likely to be somewhere between these two possibilities, and can be considered as a hybrid of these two situations in which the holding force of the bead is somewhere between the holding force of a bead with charges concentrated in one area and the holding force of a bead with the charges distributed throughout the bead.

If all the charges on the bead are concentrated in a small area, the charges on the bead are attracted by the charges of the electrostatic chuck and are therefore not seen by other beads. Thus, the repulsive force between one bead and another bead is minimal.

If the holding force F exerted by the electrostatic chuck on the bead is approximated as arising from point charges concentrated in small areas, then:

$$F = \frac{QA'}{A} \frac{q}{4\pi\epsilon_0 \epsilon_r d^2} = \frac{VD^2 q}{4 d^3}, \text{ with } A' = \pi D^2/4 \quad (4)$$

where D=the diameter of the opening in the upper conductive layer of the chuck and A' is the area of the opening.

When comparing F with a gravitational force mg, the relationship between F and the force N is as follows:

$$N = \frac{F}{mg} = \frac{VD^2}{4 d^3 g} \frac{q}{m} \quad (5)$$

wherein N is the ratio of the attractive force to the force of gravity, therefore if N is greater than about 1, the force will hold the object against gravity. The term m can be substituted since m=$4\pi\rho D'^3/3$ where $\rho$ and D' are the density and diameter of the bead, respectively. Assuming that the surface charge density $\sigma$ is a material characteristic of the beads, then q=$\sigma\pi D'^2$ and q/m=$3\sigma/4\rho D'$. Equation 5 can be rewritten as follows:

$$N = \frac{F}{mg} = \frac{3D^2 \sigma}{16 d^3 g \rho D'} V \quad (6)$$

When a second bead is attached to the same opening or via, the distance of the second bead to the shielded charge from the lower conductive layer is at least D'/2 longer than d. The attractive force is then at least a factor of $(D'/2d+1)^2$ smaller. Additionally, the effective charge seen by the second bead is q smaller. Therefore, the attractive force is smaller by another factor of $1-4Aq/Q\pi D'^2$. The attractive force F' for the second bead is as follows:

$$F' = \frac{VD^2 q}{4d^3} \frac{1 - \frac{4Aq}{Q\pi D'^2}}{\left(\frac{D'}{2d}+1\right)^2} = F \frac{1 - \frac{4Aq}{Q\pi D'^2}}{\left(\frac{D'}{2d}+1\right)^2} \quad (7)$$

Note than F is always bigger than F'. Assuming that q/m is the same for the second bead, N' for the second bead is as follows:

$$N' = \frac{F}{mg} = \frac{3D^2\sigma}{16d^3g\rho D'} \frac{1 - \frac{4Aq}{Q\pi D'^2}}{\left(\frac{D'}{2d} + 1\right)^2} V \quad (8)$$

If one and only one bead is to be picked up by the opening or via, the holding force for the second bead must be smaller than gravity. That is N' is smaller or equal to 1, or, equivalently:

$$0 \leq V \leq \frac{16d^3g\rho D'}{3D^2\sigma} \frac{\left(\frac{D'}{2d} + 1\right)^2}{1 - \frac{4Aq}{Q\pi D'^2}} \quad (9)$$

Note that Q is dependent on V. Hence, to determine whether the electrostatic chuck can attract only one bead per hole or via, equation 9 must have a solution. Calculations with practical numbers have revealed that the holding force can be readily achieved in excess of 1000 times higher than gravity, and these calculations are provided below.

If the charges are uniformly distributed over the bead, on the other hand, the charges of each bead can see each other or even come into contact with each other. The repulsive force between beads is maximal. In practice, no two beads can be closer than 2 mm apart if there is not a stronger electrostatic force to hold them together. However, the size of D' is always bigger than D so that there is no stronger force than the repulsive force. Hence, no second bead can attach the via in this case.

Using the center of the bead as the origin, and the vector $\vec{r}$ as a point on the surface of the bead, with the vector $\vec{r}'$ pointing at the surface of the lower conductive layer under the opening or via, and wherein σ and σ' are the charge density on the bead and the lower conductive layer, respectively, then the following equations apply:

$$dq = \frac{\sigma D^2}{4} d\theta d\phi \quad (10a)$$

$$\vec{r} = x\hat{i} + y\hat{j} + z\hat{k} \quad (10b)$$

$$dq' = \sigma' r' d\theta dr \quad (11a)$$

$$\vec{r}' = x'\hat{i} + y'\hat{j} - \left(\frac{D'}{2} + d\right)\hat{k} \quad (11b)$$

Hence, the holding force F on the bead is:

$$F = \frac{1}{4\pi\epsilon_0} \int\int_{beadtransporter} \frac{1(\vec{r}-\vec{r}')\cdot\hat{k}}{|\vec{r}-\vec{r}'|^2|\vec{r}-\vec{r}'|} dq'dq \quad (12a)$$

$$F = \frac{1}{4\pi\epsilon_0} \frac{\sigma\sigma'D^2}{4} \int_0^{D/2}\int_0^{2\pi}\int_0^{2\pi}\int_0^{\pi/2} \frac{r'\left(z+d+\frac{D'}{2}\right)}{|\vec{r}-\vec{r}'|^3} d\phi d\theta d\theta' dr' \quad (12b)$$

Substituting polar coordinates into the equations:

$$|\vec{r}-\vec{r}'|^2 = \frac{D^2}{2} + r'^2 - D'r'\cos(\theta - \theta') + d\sin\phi\left(\frac{D'}{2} + d\right) + D'd + d^2 \quad (13)$$

After a few approximation steps assuming the least favorable possible values assuming the lowest holding force, and setting D'/D=3, equation 12 is simplified to the following:

$$F \geq \frac{1}{4\pi\epsilon_0} \frac{\sigma\sigma'D^2}{36}$$

If it is assumed that σ and σ' have values of 17 nC/4 mm² which are readily achievable in practice, the holding force would be around 2900 times stronger than the force of gravity for a 300 μm diameter bead. A smaller bead will have a stronger holding force. Therefore, the holding force is also strong enough for a smaller bead with a diameter less than 300 μm.

The following calculations illustrate the use of practical numbers in the mathematical derivations.

If the bead carries a positive charge q, the capacitance $C_c$ of the chuck is as follows:

$$C_c = \frac{\epsilon_0\epsilon_r A}{d}$$

where d=thickness of insulating dielectric layer, and $\epsilon_r$=relative dielectric strength or dielectric constant. The capacitance surface density is:

$$\frac{C_c}{A} = \frac{\epsilon_0\epsilon_r}{d}$$

where Q=CV (V is voltage across dielectric layer). The charge density is:

$$\frac{Q}{A} = \frac{C_cV}{A} = \frac{\epsilon_0\epsilon_r V}{d}$$

If the holding force (F) on the bead is approximated as being due to point changes, then the following equation applies:

$$F = \frac{\epsilon_0\epsilon_r V}{d} \cdot \frac{\pi D^2}{4} \cdot \frac{q}{4\pi\epsilon_r\epsilon_0 d^2} = \frac{VD^2q}{4d^3}$$

Comparing this force with the following gravitational force:

$$\frac{F}{mg} = \frac{VD^2}{4d^3g} \frac{q}{m}$$

If d=2 mil=50 μm=5×10⁻⁵ m and D=100 μm=1×10⁻⁴ m, then $$\frac{q}{m} = \frac{1\,\mu C}{g} = \frac{1\,mC}{kg}$$

and $$\frac{F}{mg} = V \cdot \frac{1 \times 10^{-8}}{1.25 \times 10^{-13} \times 4 \times 9.8} \cdot \frac{1 \times 10^{-3}}{1}$$

which is approximately equal to 2 volts for d=50μ. V can be as large as 8000 V and the maximum ratio to gravitational force is 16000 since the Van der Waals force is much smaller than the electrostatic force for an object larger than 10 μm. Reversing voltage will definitely repel the bead away, thereby providing a releasing mechanism.

If a second bead approaches the same opening, the distance is at least $50 \times \sqrt{2}$ μm away.

The attractive force will be at least $$\left(\frac{50\sqrt{2}+50}{50}\right)^2 \times \text{weaker V} \left(\frac{\sqrt{2}\,R+d}{d}\right)^2$$

which is ≈6 times weaker for the second bead. However, the charge q of the first bead shields the opposite charge on the lower conductive layer.

There is therefore another factor in which the existing bead attracted to an opening reduces the charge of the chuck at the opening by a charge reducing factor of $$\frac{\left(\frac{Q}{A}\frac{\pi D^2}{4}-q\right)}{\left(\frac{Q}{A}\frac{\pi D^2}{4}\right)}$$

Therefore, the new force Fn for holding a second bead is $$6 \times \frac{\frac{Q}{A}\frac{\pi D^2}{4}}{\frac{Q\pi D^2}{4A}-q}$$

times smaller than F. Therefore, $$\frac{F}{Fn} = 6 \times \frac{\frac{\epsilon_0\epsilon_r V}{d}\frac{\pi D^2}{4}}{\frac{\epsilon_0\epsilon_r V\pi D^2}{4}-q}$$

$$2V = 6 \times \frac{\frac{\epsilon_0\epsilon_r V\pi D^2}{4d}}{\frac{\epsilon_0\epsilon_r V\pi D^2}{4d}-q}$$

$$2V = \left(\frac{\sqrt{2}\,r+d}{d}\right)^2 \times \frac{\frac{\epsilon_0\epsilon_r V}{4d}\pi D^2}{\frac{\epsilon_0\epsilon_r V}{4d}\pi D^2-q}$$

$$\frac{\epsilon_0\epsilon_r V}{4d}\pi D^2 - q = \left(\frac{\sqrt{2}\,r+d}{d}\right)^2 \frac{\epsilon_0\epsilon_r}{8d}\pi D^2$$

$$V = \left(\frac{\sqrt{2}\,r+d}{d}\right)^2 + \frac{4qd}{\epsilon_0\epsilon_r\pi D^2}$$

$$\left(\frac{\sqrt{2}\,r+d}{d}\right)^2 = 6, \epsilon_r = 2, q = 1 \,\mu C/g \times (-4\,\mu g)$$

Then $$V = \frac{3}{2} + \frac{4 \times 4 \times 10^{-12} \times 50 \times 10^{-6}}{8.85 \times 10^{-12} \times 2 \times 3.14 \times 10^{-8}}$$

and V is approximately equal to 13.3 kV, which is the applied voltage necessary to hold a second bead. The use of an applied voltage less than 13.3 kV will therefore cause approximately one bead to be attracted to each opening.

Thus, in the above example, the holding force is about 2660 times stronger than the gravitational force.

Assuming that the charges are uniformly distributed throughout the entire beads, the force holding the bead to the electrostatic chuck can be approximated as follows. If the center of the bead is the origin and D is the diameter of the bead, D' is the diameter of the opening of the chuck onto which the bead is adhered, $e\acute{O}$ is the charge density on the surface of the bead, the vector $\vec{r}$ originates at the origin in the center of the bead and points to the surface of the bead, and the vector $\vec{r}'$ originates at the origin in the center of the bead and points to the surface of the chuck, the following equation applies:

$$\vec{r} = x\hat{i} + (y'+b)\hat{j} - \left(\frac{D}{2}+d\right)\hat{k}$$

where B=0 for the first bead and B=D/2 for a second bead.

$$\vec{r}' = x\hat{i} + y\hat{j} + z\hat{k}$$

$$dq' = \sigma' r' d\theta' dr'$$

$$dq = \frac{\sigma D^2}{4} d\theta d\phi$$

$$F = \frac{1}{4\pi\epsilon_0} \iint \frac{dq\,dq'}{|\vec{r}-\vec{r}'|^2} \cdot \frac{(\vec{r}-\vec{r}')\cdot\hat{z}}{|\vec{r}-\vec{r}'|}$$

Therefore, the holding force F can be calculated by the following equation:

$$F = \frac{1}{4\pi\epsilon_0}\frac{\sigma'\sigma D^2}{4} \iiiint \frac{r'dr'd\theta'd\theta d\phi\left(z+11\frac{D}{2}+d\right)}{|\vec{r}-\vec{r}'|^3}$$

which can be integrated as follows:

$$0 \leq r' \leq \frac{D'}{2},\; 0 \leq \theta' \leq 2\pi,\; 0 \leq \theta \leq 2\pi$$

$$0 \leq \theta \leq \frac{\pi}{2}$$

$$z = \frac{D}{2}\sin\phi$$

$$x = \frac{D}{2}\cos\phi\cos\theta$$

$$y = \frac{D}{2}\cos\phi\sin\theta$$

$$x' = r'\cos\theta'$$

$$y' = r'\sin\theta'$$

Therefore, the following equations apply:

$$\vec{r}-\vec{r}' = \left(\frac{D}{2}\cos\phi\cos\theta - r'\cos\theta'\right)\hat{i} +$$

$$\left(\frac{D}{2}\cos\phi\sin\theta - r'\sin\theta - B\right)\hat{j} + \left(\sin\phi+\frac{D}{2}+d\right)\hat{k}$$

$$\therefore |\vec{r}-\vec{r}'|^2 = \frac{D^2}{4}\cos^2\phi\cos^2\theta - Dr'\cos\theta'\cos\phi\cos\theta +$$

$$r'^2\cos^2\theta' + \frac{D^2}{4}\cos^2\phi\sin^2\theta - Dr'\sin\theta\cos\phi\sin\theta -$$

-continued $$BD\cos\phi\sin\theta + r'^2\sin^2\theta' + 2r'B\sin\theta' + B^2 + \frac{D^2}{4}\sin^2\phi +$$

$$\left(\frac{D}{2}+d\right)^2 + D\sin\phi\left(\frac{D}{2}+d\right) = \frac{D^2}{4} + r'^2 -$$

$$Dr\cos\phi\cos(\theta - \theta') + D\sin\phi\left(\frac{D}{2}+d\right) + \frac{D^2}{4} +$$

$$Dd + d^2 + B^2 + 2r'B\sin\theta' - BD\cos\phi\sin\theta$$

$$|\vec{r}-\vec{r'}|^2 \leq \frac{D^2}{4} + r'^2 + Dr' + D\left(\frac{D}{2}+d\right) + \frac{D^2}{4} +$$

$$Dd + d^2 + B^2 + 2r'B + BD = r'^2 + 2r'B + C \text{ where } C =$$

$$D^2 + 2Dd + d^2 + B^2 + BD$$

$$\therefore F \leq$$

$$\frac{1}{4\pi\epsilon_0} \frac{\sigma'\sigma D^2}{4} \iiint \frac{r'dr'd\theta'd\theta d\phi \left(\frac{D}{2}\sin\phi + \frac{D}{2} + d\right)}{(r'^2 + 2r'B + C)^{\frac{3}{2}}} =$$

$$K\left(\frac{D}{2} + \frac{\pi D}{4} + \frac{\pi d}{2}\right) \iiint \frac{r'dr'd\theta'd\theta}{(r'^2 + 2r'B + c)^{\frac{3}{2}}} \quad \left[K = \right.$$

$$\left.\frac{1}{4\pi\epsilon_o} \frac{\sigma'\sigma D^2}{4}\right] = K\left(\frac{D}{2} + \frac{\pi D}{4} + \right.$$

$$\left.\frac{\pi d}{2}\right) 4\pi^2 \int_0^{\frac{D'}{2}} \frac{r'dr'}{(r'^2 + 2r'B + C)^{\frac{3}{2}}} \quad \because r' \equiv D'/2$$

$$\therefore F > K\left(\frac{D}{2} + \frac{\pi D}{4} + \right.$$

$$\left.\frac{\pi d}{2}\right) 4\pi^2 \int^{\frac{\bar{D}}{2}} \frac{r'dr}{\left(\frac{D'^2}{4} + D'B + C\right)} =$$

$$K\left(\frac{D}{2} + \frac{\pi D}{4} + \frac{\pi d}{2}\right) 4\pi^2 \frac{\frac{D'^2}{8}}{\left(\frac{D'^2}{4} + D'B + C\right)^{\frac{3}{2}}}$$

$$C = 2D^2 \text{ for } B = \frac{D}{2} \text{ (second bead)} = D2 \text{ for } B = 0$$

$$F \cong \geq K\left(\frac{d}{2} + \frac{\pi D}{4} + \frac{\pi d}{2}\right) \cdot \frac{\pi^2 D^2}{2D^3\sqrt{8}} \geq$$

$$\frac{KD^2}{D^2} = \frac{K}{q} = \frac{1}{4\pi\epsilon_o} \frac{\sigma'\sigma D^2}{36}$$

One of the conductive layers, such as the lower conductive layer of the electrostatic chuck, can be made x-addressable or x-y-addressable such that the location of the objects attracted to the chuck can be selected. For example, in an x-addressable chuck, the lower conductive layer has rows of openings in which a single row can be activated at one time. Thus, one can select the placement of objects only on a specific row of openings of the electrostatic chuck, rather than on every opening or row or of the chuck. In an x-y-addressable chuck, the area of the lower conductive layer corresponding to each opening or via can be made independent of the remainder of the lower conductive layer corresponding to any of the other openings. Thus, for example, one can select the placement of objects only on specific openings of the electrostatic chuck, rather than on every opening of the chuck.

In certain preferred embodiments, the objects to be applied to the chuck are charged prior to their application. The charge can be, for example, either a plasma charge or an electrostatic charge, depending upon the nature of the object to be applied to the chuck. For instance, when using beads, either a plasma or electrostatic charge can be used since neither causes damage to the bead. For other objects that may be damaged by plasma charging, electrostatic charging is preferably used. Examples of materials that can be used for tribocharging include teflon, and polymers of chlorotrifluoroethylene, chlorinated propylene, vinyl chloride, chlorinated ether, 4-chlorostyrene, 4-chloro-4-methoxy-styrene, sulfone, epichlorhydrin, styrene, ethylene, carbonate, ethylene vinyl acetate, methyl methacrylate, vinyl acetate, vinyl butyral, 2-vinyl pyridine styrene, nylon and ethylene oxide. See, for example, "Triboelectrification of Polymers" in K. C. Frisch and A. Patsis, *Electrical Properties of Polymers* (Technomic Publications, Westport, Conn.), which article is hereby incorporated by reference in its entirety.

Preferably, excess objects that are not electrostatically adhered to the chuck are removed before transferring the objects to a substrate. To release the objects, the application of voltage can be stopped, or for greater force of removal, the voltage can be reversed.

In addition to providing the chucks themselves, the present invention also provides methods of using the chucks. For example, in one aspect, the present invention provides methods for electrostatically holding an object or multiple objects, comprising (a) providing an electrostatic chuck; (b) applying a power source to the chuck; and (c) applying objects to the chuck, thereby attracting the objects to the chuck. In certain embodiments, step (b) comprises (i) applying a voltage having a polarity to a first conductive layer of the chuck, the first conductive layer being on top of vias extending through a layer of the chuck; and (ii) applying a voltage of opposite polarity to a second conductive layer of the chuck below the vias, thereby inducing a charge of one polarity on the bottom of the vias and a charge of the opposite polarity on the top of the vias, whereby the polarity of the top of the via is opposite in polarity to the charge of most of the objects to be attracted to the chuck. In preferred embodiments, the conductive layers are made of metal.

In preferred embodiments, the methods include electrostatically charging the object before applying it to the chuck. This can be accomplished through friction, for example, by mechanically shaking a mixture of beads and a powder, preferably for about 30 minutes, and preferably with an amount of beads and powder that so that the surface area of the beads corresponds to the surface area of the powder, where the surface area can be determined by calculating $4\pi r^2$. For example, about 15 g of beads can be used for about 450 mg of powder, assuming the density is about 1 g/cc. The beads preferably are a conductive material, such as steel, coated by a dielectric, such as Teflon or Kynar. Teflon coated beads can be obtained, for example, from Nu-Kote (Derry, Pa.) and Kynar coated beads can be obtained, for example, from Vertex Image Products (Yukom, Pa.).

In addition to being used to position objects, the chucks of the present invention, including the chucks designed for positioning objects, can be used to simply hold an object. Further, in addition to beads, the chucks of the present invention can be used for powders and tablets, as described below. Additionally, the chucks of the present invention can be used for numerous other types of objects, including but not limited to a thin conductive substrate such as an edible polymeric substrate, which can be used as a substrate for deposition of a pharmaceutically active powder, and the substrate can subsequently be used, for example, to create or coat a tablet.

The chucks of the present invention can be used to hold an object or multiple objects against gravitational forces during chemical or pharmaceutical processing. Additionally, the present invention provides methods of chemical manufacturing using a chuck to attract an object or multiple objects to a substrate, the objects being used in chemical manufacturing. In another aspect, the present invention provides methods of manufacturing a pharmaceutical composition by using a chuck to attract an object or multiple objects to a substrate, the objects being used to manufacture the pharmaceutical composition. The chuck can be manufactured to have an increased size in order to attract an object having an increased surface area.

Preferably, the thickness of an object held by an electrostatic chuck of the present invention is less than about 300 mm, and more preferably, less than about 100 mm, even more preferably, less than about 50 mm, even more preferably, less than about 25 mm, even more preferably, less than about 10 mm, even more preferably, less than about 5 mm, and most preferably, less than about 3 mm.

In certain preferred embodiments, the objects held by a chuck are pharmaceutical substrates, and the objects are round, such as tablets. Alternatively, for example, the objects are oblong, and can be, for example, capsules or caplets. When the object is a tablet, preferably it has a thickness no greater than about 3 mm. The present invention additionally provides for the use of a chuck to hold an object or objects which, in some embodiments, are coated with particles while being held. In preferred embodiments, the particles are within a powder comprising a pharmaceutically active compound.

Thus, in addition to beads, the chucks of the present invention can be used to hold a substrate for application of a pharmaceutically active ingredient. Such substrates include, for example, a suppository, or an edible substrate such as a pharmaceutical tablet, capsule or caplet or a water soluble film such as a hydroxypropyl methyl cellulose resin. Other substrates include dressings, bandages and patches, as well as, for example, a container for an inhaler. For example, the inhaler can be a flat, ceramic disk upon which a plurality of medicament dosages are positioned. See, for example, U.S. Ser. No.08/471,889, which is incorporated herein by reference.

Further, the present invention provides an electrostatic chuck comprising a configuration for depositing a selected number of objects onto a recipient substrate. Preferably, the objects are less than about 3 mm in thickness, and the configuration of the chuck preferably comprises a conductive layer having an x or y-addressable area for depositing a selected number of objects onto the recipient substrate. Preferably, the chuck has multiple areas that are x- or y-addressable, each area preferably corresponding to a separate substrate such as a pharmaceutical carrier. In preferred embodiments, the objects are deposited substantially simultaneously onto multiple substrates, and in certain embodiments, the substrates are connected. For example, the substrates can be a pharmaceutical carrier and the objects can be, for example, particles in a powder, microspheres or liposomes which contain a pharmaceutically active ingredient, and together they create a pharmaceutical dosage form. When the substrates are connected, a multidosage pack can be formed in which the dosage decreases, for example, from one unit to the next, such as with a multidosage pack for birth control. The dosage can be determined by the number of objects placed into each pharmaceutical carrier using an electrostatic chuck. Thus, the present invention provides a multidosage form having units in which each unit has a dosage, at least two units having different dosages, the dosages being determined by the number of microspheres in the unit. In certain preferred embodiments, the microspheres are from about 1 to about 500 microns, in some instances, preferably about 100 to 500 microns, and in other instances, preferably about 50 microns.

Figure 26:
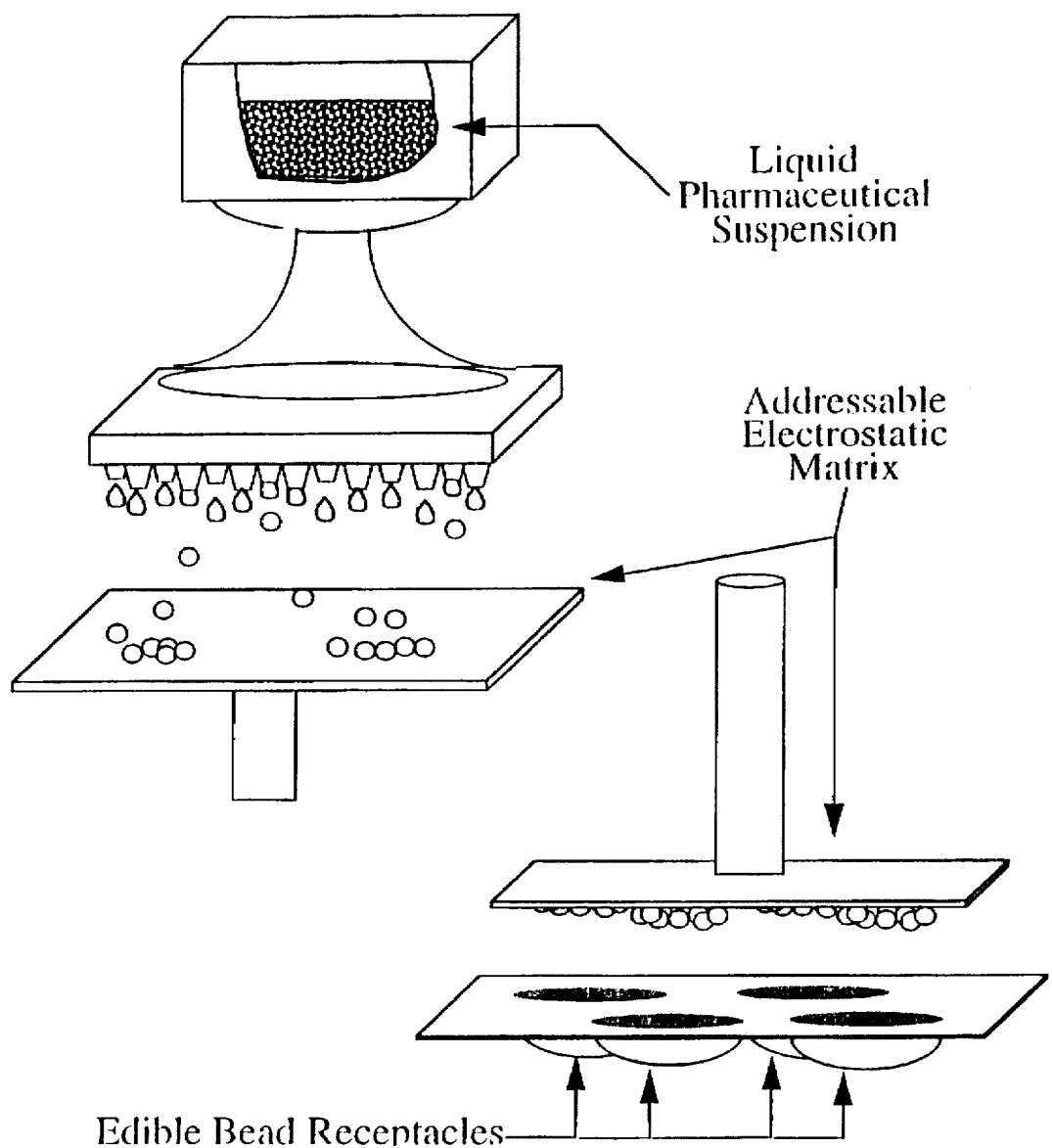
FIG. 26 is a schematic diagram of an electrostatic chuck of the present invention for creating multi-dosage units.

Preferably, the microspheres comprise a pharmaceutically acceptable polyalkylene, such as polyethylene glycol, which is preferably at a concentration of at least about 90%, and more preferably, about 95% polyethylene glycol. The chucks described below such as for attracting tablets, for example, and for creating charge images, with another dielectric layer, can be used for creating the above described multidosage forms. See, for example, FIG. 26.

In addition to pharmaceutical objects or particles, the electrostatic chucks of the present invention can be used to attract any other particle that can be adhered to an electrostatic chuck. Additionally, for example, the chucks can be used to attract and deposit liposomes into capsules for cosmetics.

Furthermore, the electrostatic chucks can be scaled up for large scale continuous manufacturing, such as using a sheet of an edible substrate for use with tablets, for example, or a sheet of an inhaler substrate.

In addition to the chucks, the present invention also provides methods for depositing a selected number of objects comprising:
 (a) providing an electrostatic chuck having an area that is x- or y-addressable;
 (b) contacting the chuck with objects, wherein the objects substantially adhere to the chuck in the areas that are x- or y-addressable; and
 (c) releasing the objects onto a recipient substrate aligned with the areas of the chuck on which the objects are adhered. The present invention also provides methods for producing a dosage form comprising:
  (a) providing an electrostatic chuck having an area that is x- or y-addressable;
  (b) contacting the chuck with particles comprising a pharmaceutically active ingredient, wherein the particles substantially adhere to the chuck in the areas that are x- or y-addressable; and
  (c) releasing the particles onto a pharmaceutical carrier aligned with the areas of the chuck on which the particles are adhered.

Furthermore, a pharmaceutical or other substrate held by an electrostatic chuck, for example, can be coated with a powder, such as a powder having a pharmaceutically active ingredient. Preferably, the powder is in dry micronized form, using for example, an air jet milling process, and the particles are at least about 1 micron in diameter, and preferably from about 1 to about 10 microns, and more preferably about 4 to about 8 microns in diameter. Preferably, the powder is electrostatically charged before application to the chuck, for example, through admixture with beads such as by mechanical shaking. The shaking time is preferably about 30 minutes, and the amount of beads used is preferably calculated so that the surface area of the beads is proportional to the surface area of the particles of the powder. For example, 15 grams of beads can be used with 450 mg of powder.

Without being limited to a particular theory, the electric potential generated by the electrostatic chucks of the present invention is believed to serve both for holding a conductive object in place, such as a tablet, and for attracting a charged object, such as particles within a powder, onto a recipient substrate.

When using a chuck of the present invention to hold a recipient substrate, such as a tablet, during deposition of particles, such as a powder containing a pharmaceutically active ingredient, the tablets are preferably closely packed on the chuck so that only the tablets receive the powder, and the chuck itself is not coated with powder. For example, the electrostatic chucks of the invention can be used to hold about eighty-one tablets in a row of nine tablets by a column of nine tablets.

The size of the chuck depends upon the number and size of objects to be attracted using the chuck. For example, a 2 inch by 2 inch chuck can hold about 100 tablets in which each tablet has a diameter of about 5.6 mm. Preferably, the chuck is reusable and can be washed between uses.

Advantages of the present invention include the ability to hold a pharmaceutical substrate without the use of a mechanical means. Thus, for example, the present invention provides an electrostatic mechanism for holding a tablet that is loosely compressed and that would crumble if held by mechanical means or by a vacuum chuck. Additionally, for example, without being held to a particular theory, it is believed that the pharmaceutically acceptable carriers, for example, in tablets are frequently conductive and dissipate their charge within less than about a millisecond. An electrostatic chuck provides an advantage by maintaining the charge of a pharmaceutical substrate that would otherwise lose its charge.

Preferably, the tablets include a substantial amount of cellulose, preferably greater than about 50% cellulose, more preferably greater than about 60% cellulose, even more preferably greater than about 75% cellulose, even more preferably greater than about 90% cellulose, and most preferably about 95% cellulose. In other embodiments, the tablets include about 65% lactose and about 34% cellulose. In certain embodiments, the tablets include about 80% lactose. Preferably, the tablets do not have an ingredient which would cause them to deviate from being either a good conductor or a good dielectric. For example, with a conductive tablet such as one that is substantially made of cellulose, preferably the tablet does not include dielectric metal oxides such as ferrous or ferric oxide or titanium oxide. Preferably the amount of iron oxide, if present, is less than about 1%. Additionally, the tablet preferably does not include moisture and preferably does not include a substantial amount of a salt such as sodium bicarbonate that becomes conductive with high humidity, thereby making the most efficient operation of the electrostatic chuck affected by humidity.

The tablets may optionally have additional components, including but not limited to sodium starch glycolate and magnesium stearate.

When an edible substrate, having for example, a pharmaceutically active powder deposited onto it, is fused with a tablet, preferably the edible substrate is made of substantially the same component as the tablet, such as cellulose. For example, hydroxypropyl methyl cellulose can be used, such as Edisol M Film M-900 or EM 1100 available from Polymer Films Inc. (Rockville, Conn.).

Preferably, the density of the tablet is such that if it has a diameter of about 5.6 mm, the tablet weighs no more than about 100 mg. If the diameter of the tablet is twice as large, the weight can be proportional to the square of the diameter.

The conductivity of a tablet can be determined by measuring the d.c. impedance, by placing the tablet in an electrical circuit between a voltage source and a picoammeter. The capacitance of the tablet can be measured by placing the tablet sample in parallel with a Hewlett Packard 4192A Low Frequency Impedance Analyzer set for 1 kHz. The tablets are preferably painted on both sides with a thin layer of conductive silver paint to ensure good electrical contact. Several formulations were tested, and conductivities between $2.4 \times 10^9 \Omega$ and $6.3 \times 10^9 \Omega$ were found. The range of impedance was about $2 \times 10^9 \Omega$ to $23 \times 10^{10} \Omega$. The capacitance was determined to be 0.3 pF to 0.5 pF, which correspond to a charge retention time of 100 μsec. to 1 msec.

In addition to the chucks described above for specifically positioning multiple objects for transfer onto a recipient substrate, the present invention also provides electrostatic chucks that are used to hold an object or multiple objects during processing in the chemical or pharmaceutical industry. Such processing includes the deposition of particles on the objects, such as the deposition of a pharmaceutically active powder on tablets. This is particularly useful, for example, when the active ingredient is incompatible with the remainder of the tablet. Furthermore, more than one type of ingredient can be coated on an object, such as a tablet. The tablet can be further processed after the particles are deposited on it; for example, the tablet can be coated after deposition.

In one aspect, the present invention provides an electrostatic chuck comprising a conductive layer forming at least one electrode for electrostatically attracting multiple objects. In other preferred embodiments, the chuck comprises a conductive layer forming two electrodes, which, in certain embodiments, are serpentine or interdigitated and provide for a higher probability that the area of the two electrodes covered by the same object are the same, therefore objects at different locations of the chuck are held at the same potential. Additionally, the surface area is beneficially inversely proportional to the object to be held by the chuck. For example, in preferred embodiments, the electrode has a larger surface area to electrostatically hold a smaller object. The conductive layer that attracts or adheres objects to the chuck is termed an "upper conductive layer", and this layer is not necessarily the outermost layer of the chuck. For example, the upper conductive layer can have a thin dielectric layer on top of it, between the conductive layer and the objects. Further, the chuck may have more than one conductive layer forming an electrode, although only the conductive layer that attracts or adheres objects to the chuck is termed an "upper conductive layer".

In certain preferred embodiments, the electrostatic chucks are made of solid state materials such as glass or silicon dioxide or other ceramics which impart good dielectric strength and therefore better attraction of objects. The better dielectric strength also provides for a thinner layer, and a lower voltage which increases safety. Further, the materials are well-characterized, durable, mechanically strong and readily available.

In certain preferred embodiments, the chuck comprises four layers. The lower conductive layer is optional, and is present in preferred embodiments. Preferably, the lower conductive layer is electrically floating. The lower conductive layer can be made, for example, of metal, such as aluminized polypropylene, and is preferably about 500 nm in thickness. Without being limited to a particular theory, it is believed that the lower conductive layer enhances the fringing field on top of the electrostatic chuck thereby causing charge redistribution of the object attracted to the chuck, which provides for a stronger electrostatic attraction of an object to the chuck.

The second layer, on top of the lower conductive layer, is a dielectric layer, such as polypropylene, or a semiconductive layer, such as a ceramic, for example, $SiO_2$. The third layer is an upper conductive layer on top of the dielectric layer, and this upper conductive layer has at least one electrode, such as two interdigitated electrodes, which are preferably made of a metal, such as silver. Preferably, the upper conductive layer is made of a material that does not negatively affect pharmaceutically active materials.

The fourth layer, on top of the upper conductive layer, is an optional thin dielectric layer, which is preferably made of polyimide or another material of high dielectric strength, and preferably has a thickness of about 10 microns to about 50 microns.

Figure 6:
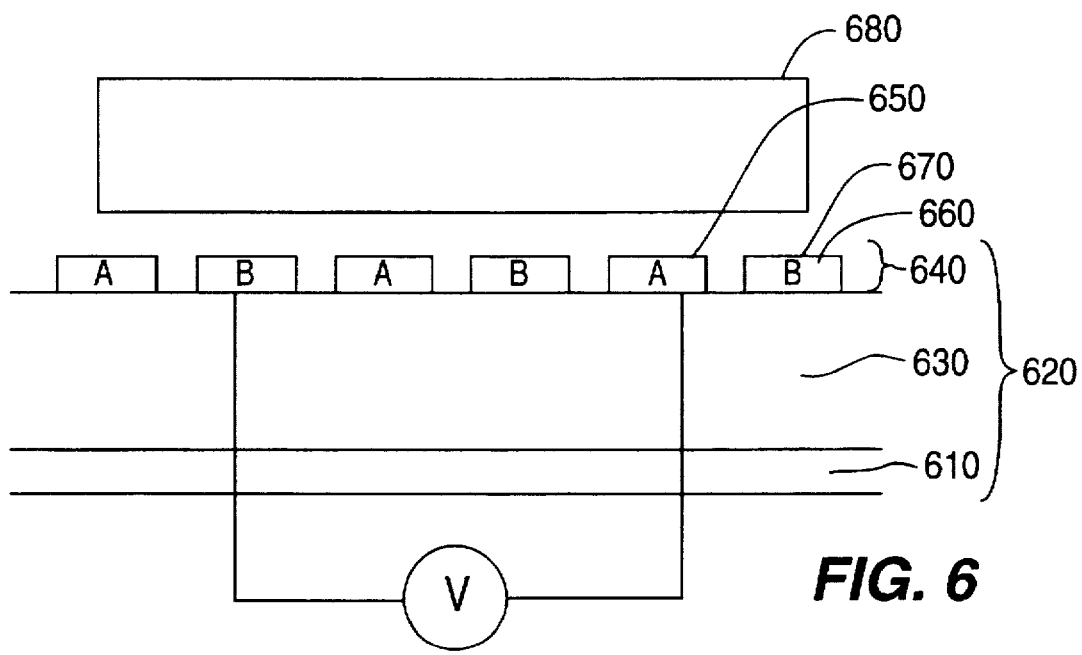
FIG. 6 is a cross-sectional view of a schematic representation of an electrostatic chuck with interdigitated electrodes according to the present invention.
Figure 7:
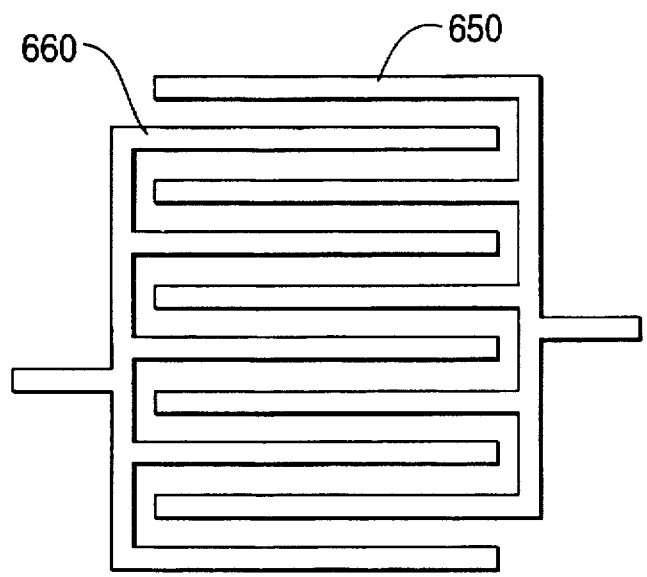
FIG. 7 is a top view of a schematic representation of the interdigitated electrodes of FIG. 6.

Referring to FIG. 6, the lower conductive layer 610 of the chuck 620 is coated with a dielectric layer 630. On top of the dielectric layer is an upper conductive layer 640 forming an interdigitated electrode, with a first electrode 650 and a second electrode 660. A second dielectric layer 670 is placed on top of the upper conductive layer 640. FIG. 7 shows a top view of the two interdigitated electrodes 650 and 660. This chuck 620 can be used to attract an object 680, as shown.

During use of an electrostatic chuck having an upper conductive layer with two interdigitated electrodes, a voltage is applied across the two electrodes of the chuck, preferably about 200 to about 2000 volts. See, for example, Example 4 below. The voltage applied to an electrostatic chuck can be direct current voltage (DC) or alternative current voltage (AC) provided that the same amount of voltage is applied.

Without being limited to a particular theory, assuming a 1 mm contact area for the tablet, $$\text{Capacitance} = \frac{\epsilon_0 \epsilon_r A}{d} = \frac{8.89 \times 10^{-10} \times 1 \times 1 \times 10^{-6}}{50 \times 10^{-6}} \approx 17 pF$$

$$E = \frac{1}{2} CV^2$$

$$F = \frac{dE}{dX} = \frac{\epsilon_0 \epsilon_r A V^2}{2X^2} \approx \frac{17 \times 10^{-12} \times (500)^2}{2 \times 5^{-0} \times 10^{-6}} = 42.5 \mu N$$

For the capacitor, assuming that X=the thickness of dielectric layer, for a 60 mg tablet, the gravitational force= $60 \times 10^{-6}$ kg$\times$9.8 N/kg$\cong$600 µN and the electrostatic force is therefore about 60 times stronger than the force of gravity.

Without being limited to any particular theory, it is believed that the object need not necessarily have direct physical contact with an electrode in the upper conductive layer in order to be electrostatically held by the chuck. When using the chuck having an upper conductive layer with interdigitated electrodes to deposit a charged powder onto a tablet, for example, the electrostatic force holding the tablet increases as the charged powder is deposited on the tablet, thereby providing an additional advantage in a stronger holding force. There is a limited amount of charged powder that can be deposited using the interdigitated chuck, which is based on bias potential. Therefore, this chuck provides the advantage of the ability to determine the amount of powder deposited upon a substrate by measuring the amount of charge remaining. The charge can be measured using, for example, an electrometer or a picoammeter. The value of the charge can be used to determine the mass of the powder deposited. The design of this chuck provides for its ability to electrostatically hold virtually any object that is conductive relative to the strong dielectric layer on top of the chuck.

Figure 8A:
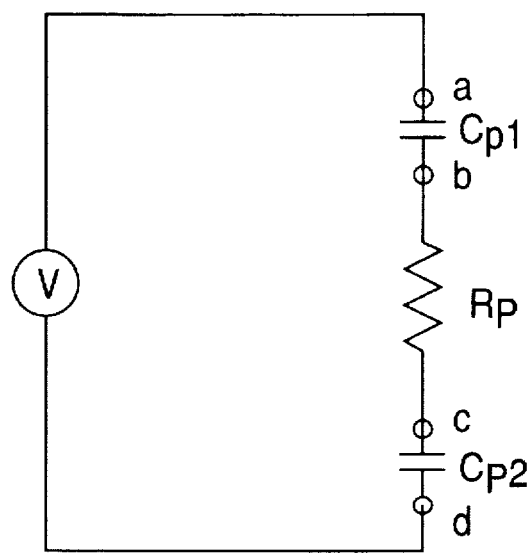
FIGS. 8A and 8B are circuit diagrams of an electrostatic chuck having two electrodes, FIG. 8A depicting the chuck without a lower conductive layer, and FIG. 8B depicting the chuck with a lower conductive layer.
Figure 8B:
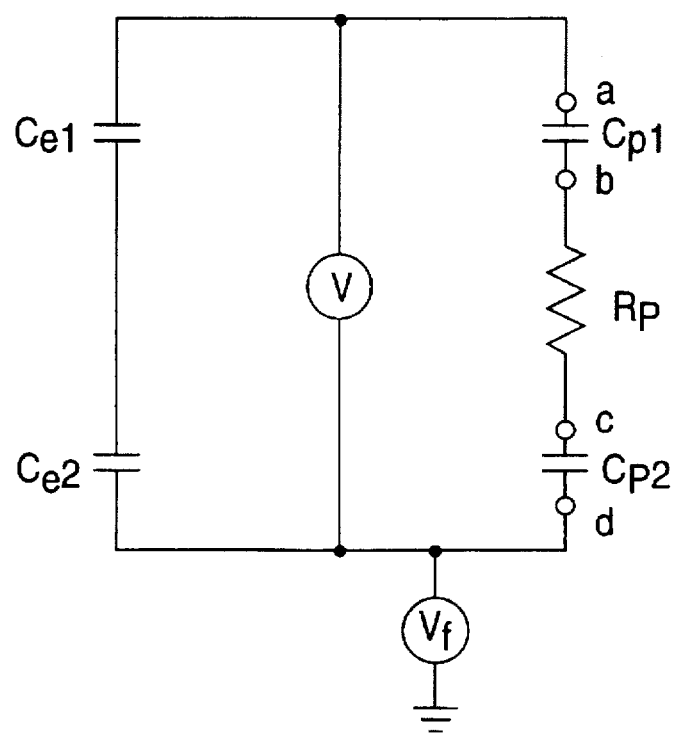

Without being limited to a particular theory, the following mathematical formulas can be used to evaluate the holding force of the electrostatic chuck illustrated in the circuit diagrams shown in FIGS. 8A and 8B. FIG. 8A represents a circuit diagram of an electrostatic chuck with an upper conductive layer having two electrodes, each electrode having an object attracted to it, and in which the lower conductive layer is absent. FIG. 8B represents a circuit diagram of a chuck with an upper conductive layer having two electrodes, each electrode having the same object attracted to it, and in which the lower conductive layer is present. $Cp_1$ is the capacitance of the capacitor formed between an object, such as a tablet, and the first electrode; $Cp_2$ is the capacitance of the capacitor formed between an object, such as a tablet, and the second electrode; Rp is the resistance due to the object; and V represents the holding potential which is related to the force holding the object onto the chuck. Referring to FIG. 8B, $Ce_1$ is the capacitance of the capacitor formed between the lower conductive layer and the first electrode; $Ce_2$ is the capacitance of the capacitor formed between the lower conductive layer and the first electrode; and $V_f$ represents the bias potential.

A conductive object and the electrode in the upper conductive layer form a capacitor with a capacitance approximately equal to $$C = \frac{\epsilon_0 \epsilon_r A}{d} \quad (1)$$

where $\epsilon_o$ is the dielectric constant of a vacuum, and $\epsilon_r$ is the relative dielectric constant of the dielectric layer on top of the electrodes in the upper conductive layer; A is the contact area and d is the thickness of the dielectric layer. The force holding of the conductive object and the electrode in the upper conductive layer is given by:

$$F = \frac{\epsilon_0 \epsilon_r A V^2}{2d^2} \quad (2)$$

where V is the voltage across the dielectric layer. Assuming $\epsilon_r$=3 for a polymer, V=350 V, d=10 µm and A=15 mm$^2$, the electrostatic force is 0.24N. If the material has a mass of 60 mg, the gravitational force is 0.59 mN. The electrostatic force is over 400 times stronger than the gravitational force.

In the circuit diagrams shown in FIGS. 8A and 8B, $V_{ad}$=V. Provided enough charging time elapsed after the voltage V is applied, $V_{bc}$=0. When charged powders land on $R_p$, the voltage across the two capacitors is rearranged. However, the power supply maintains the overall voltage drop $V_{ad}$ as a constant. In a practical design, $C_{p1}$ is approximately the same as $C_{p2}$ and $V_{ab} \sim V_{cd} \sim V/2$. The overall attractive force is proportional to $(V_{ab}^2 + V_{cd}^2) \sim V^2/2$. If the voltage on point b (or c) is altered due to the landing of the charge powders by V', the new attractive force is proportional to $V^2/2 + 2V'^2$. As a result of the addition of the charged powder, the attractive force increases. Also, normal leakage current through the two capacitors of limited resistance is supplied by the power supply as well.

The applied potential V can be maintained at a separated voltage difference $V_f$ with respect to ground. The potential at the conductive material (in this application, the conductive material is a tablet) is $V_f + V/2$. If the tablet is exposed to a cloud of charged powders, the powders will experience the field due to the potential $V_f + V/2$ and be attracted or repelled according to the sign of the charge on powder. If the resultant force is attractive, the powder will be deposited onto the tablet. Since both $V_f$ and V can be controlled in magnitude as well as the sign, the resultant force can be controlled so that it is attractive for deposition.

Without being limited to any particular theory, it is believed that before any conductive material is attached to the chuck shown in FIG. 6 and in the circuit diagram in FIG. 8, the charges will be concentrated on the edges of the electrodes. There is a relatively weak fringing electric field on the top of the electrostatic chuck. This field may not be strong enough to cause charge redistribution in the tablet for attaching the tablet to the chuck. This limitation is removed by the addition of a lower conductive layer beneath the chuck, also known as a backplane. This conductive layer causes the charges on the electrodes to redistribute more evenly across the electrodes. As a result, a higher fringing electric field on the top of the chuck and a better initial attraction between the tablet and the chuck are formed. The new equivalent circuit is shown in FIG. 8B.

Figure 27A:
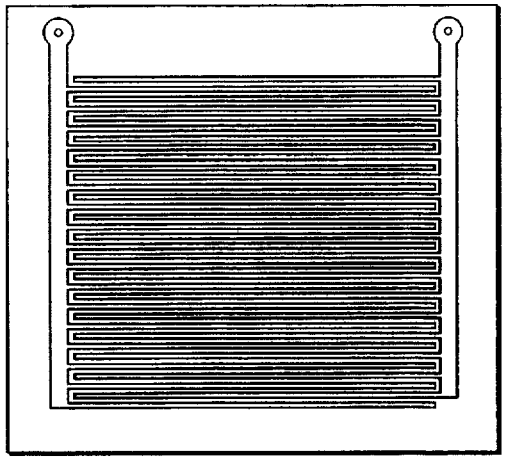
FIGS. 27A–C provide three photographs of an electrostatic chuck according to the present invention.
Figure 27B:
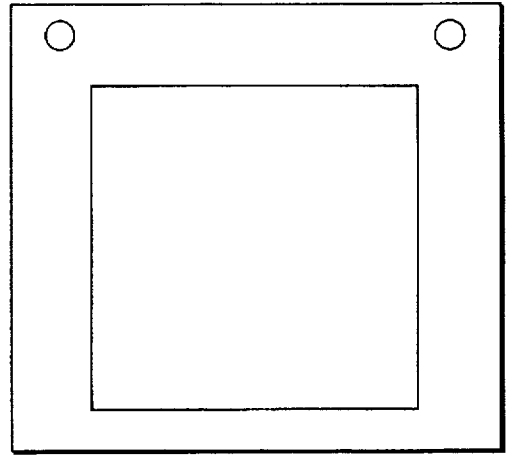
Figure 27C:
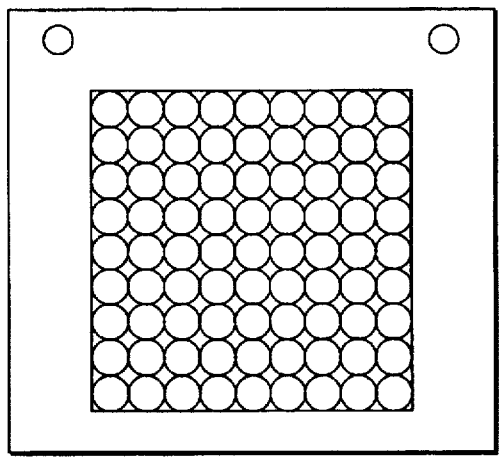

In other preferred embodiments, the chuck comprises an upper conductive layer having a single electrode. Preferably, the chuck includes three layers. The bottom layer is preferably a lower conductive layer made of metal, for example, such as aluminum. Alternatively, for example, the bottom layer can be semiconductive, such as a silicon wafer. The middle layer is a dielectric layer preferably having a high dielectric strength, such as thermally grown silicon dioxide. The top layer is an upper conductive layer forming the electrode, which can extend from the top of the dielectric layer externally, or can be embossed whereby it extends internally into the dielectric layer. The upper conductive layer is made of a conductive material, such as a metal, for example, copper wires, or a semiconductor, for example, polycrystalline silicon. Preferably, the upper conductive layer has no significantly negative effect on a pharmaceutically active compound. In preferred embodiments, the thickness of the upper conductive layer is from about 100 nm to about 500 nm. Preferably, the upper conductive layer comprises conductive stripes, and when used to attract multiple objects, the width of the area between the stripes preferably is approximately equal to the average diameter of the objects, thereby providing for complete coverage of the electrode when the maximum number of objects are held by the chuck. Thus, when the chuck is used to hold objects while particles are being deposited on the objects, this configuration provides for substantially eliminating the deposition onto the chuck itself. See, for example, FIG. 27.

Figure 9A:
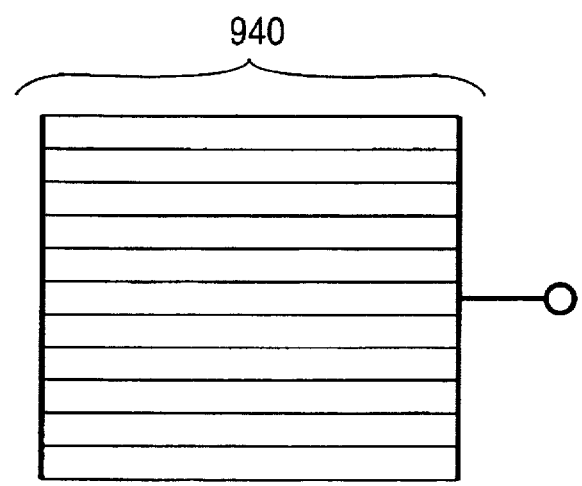
FIG. 9A is a top view of a schematic representation of the single electrode of FIG. 9B.
Figure 9B:
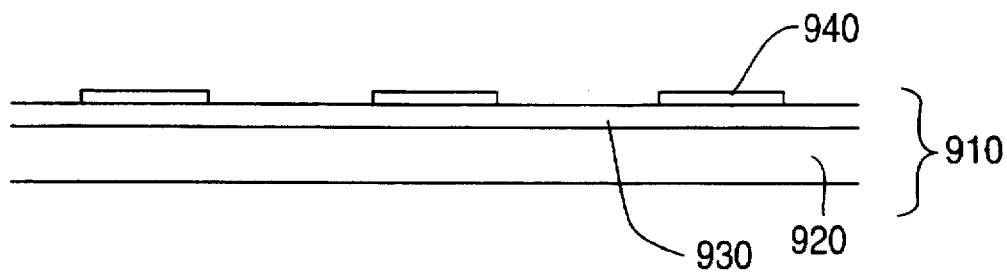
FIG. 9B is a cross-sectional view of a schematic representation of an electrostatic chuck with a single electrode on the upper conductive layer, which protrudes from the dielectric layer, according to the present invention.
Figure 9C:
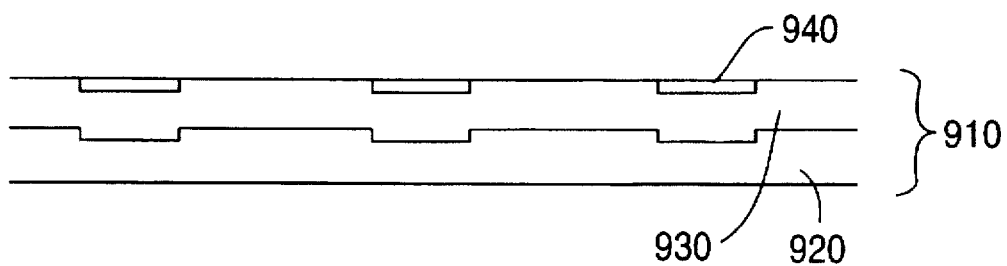
FIG. 9C is a cross-sectional view of a schematic representation of an electrostatic chuck according to the present invention with a single electrode on the upper conductive layer, which is embossed in the dielectric layer.

Referring to FIG. 9B, for example, the electrostatic chuck 910 has a lower conductive layer 920, with a dielectric layer 930 on top of it. The upper conductive layer 940 either protrudes outward from the dielectric layer 930, as shown in FIG. 9B, or is embossed into the dielectric layer 930, as shown in FIG. 9C. A top view of the striations in the upper conductive layer 940 is shown in FIG. 9A. During use of the electrostatic chuck 910, a bias potential is applied between the upper conductive layer 940 and the lower conductive layer 920.

Without being limited to a particular theory, it is believed that when the above-described chuck with a single electrode in the upper conductive layer is used, for example, to electrostatically hold tablets while a charged powder is applied to the tablets, there is no charge redistribution in the tablet, but rather, the tablet is directly charged by contact with the electrode. Therefore, an unlimited amount of charged powder can be deposited on the tablets.

In further preferred embodiments, electrostatic chucks of the invention are provided for use in charge imaging. For example, a chuck can be used for charge imaging on a substrate to determine the deposition of particles in a particular pattern on the substrate. In preferred embodiments, particles of a powder having a pharmaceutically active ingredient are deposited in a selected pattern onto a pharmaceutical substrate. Preferably, the substrate is a thin dielectric material, such as polypropylene or another thin edible substrate such as hydroxypropyl methyl cellulose, preferably having a thickness of about 25 microns. For example, a plastic substrate for use with an inhaler can be used. In addition to using a thin substrate mechanically attached to the electrostatic chuck, a substrate can be used as a recipient of the particle even when the substrate is not attachable to the electrostatic chuck, since the substrate can be held, for example, by a vacuum chuck that is behind the electrostatic chuck.

The electrostatic chucks of the invention can also be used to hold objects, for example, for the application of a design, such as a candy coating on an edible substrate. Alternatively, for example, the electrostatic chucks can be used to hold objects for the application of a dry powder paint.

In preferred embodiments for charge imaging, the electrostatic chuck comprises a floating electrode, which is used to selectively attract particles to a substrate in contact with the floating electrodes. Preferably, the substrate has physical contact with the floating electrodes. Without being limited to a particular theory, it is believed that the use of floating electrodes on the electrostatic chuck generates an image of charges by capacitive coupling. Each floating electrode has a charge which is shifted as charged particles contact the electrode. The process of deposition of charged particles on the floating electrode continues until the floating electrode can no longer shift potential, at the point in which it has the same potential as the shielding electrode, which is described below.

The electrostatic chuck with floating electrodes preferably has three layers. The bottom layer is a lower conductive layer, for example silver or copper. Alternatively, for example, the lower conductive layer can be made of a semiconductive material, such as a silicon wafer. The lower conductive layer is optional, but preferred. Without being bound to any particular theory, it is believed that the use of a lower conductive layer prevents charged particles from continuing to deposit indefinitely onto the substrate(s) held by the chuck, and in limiting the amount of particles deposited, may provide for greater uniformity of deposition.

The middle layer is a dielectric layer, such as thermally grown silicon dioxide or polyimide, and is preferably about 0.5 to about 2 mils thick. The top layer is a discontinuous electrode layer with floating and shielding electrodes that are electrically connected, but with a gap between them. The upper conductive layer can be made of, for example, a thin gold film coating, and preferably, the floating and shielding electrodes have the same thickness, which is preferably about 500 nm. In preferred embodiments, the gap between the floating electrode and the shielding electrode is from about 25 microns to about 500 microns. The shape of the floating electrode can be varied, and can be irregular, so long as the gap between the floating electrode and the shielding electrode remains substantially constant. In certain preferred embodiments, the floating electrode is round, and forms a dot that can be used to create a selected pattern. In certain preferred embodiments, the shielding electrode is grounded. The shielding electrode is biased with respect to the lower conductive layer. The polarity of the bias is preferably opposite of the powder to be deposited on the substrate.

Referring to FIG. 10, for example, the chuck 1110 has a lower conductive layer 1120, with a dielectric layer 1130 on top of it. The dielectric layer has an upper conductive layer 1140 on top of it. The upper conductive layer 1140 is electrically connected, but with a gap 1150 between a shielding electrode 1160 and a floating electrode 1170. A top view of the upper conductive layer 1140 is shown in FIG. 11, with the floating electrode 1170 in the center, and a gap 1150 between the floating electrode and the surrounding shielding electrode 1160. The area of the lower conductive layer 1120 corresponding to each floating electrode can be made addressable in rows, like the x-addressable chucking system described above, or individually addressable, like the x-y-addressable chucking system described above.

During use, a bias potential is applied between the shielding electrode and the lower conductive layer. If the particles to be deposited are positively charged, the bias potential will be negative, and if the particles to be deposited are negatively charged, the bias potential will be positive. Preferably, the shielding electrode is connected to ground. During deposition of particles, the length of time of the deposition will preferably be continued until each and every floating electrode has reached its limit in which the potential of the floating electrode matches the potential of the shielding electrode.

Using an electrostatic chuck with floating electrodes to deposit powder onto a substrate, the amount of powder deposited on the substrate is determined by the charge or bias potential of the chuck, and only a finite amount of powder can be deposited. Without being limited to a particular theory, it is believed that the deposition of powder ends when the charges on the floating electrode can no longer be redistributed, which occurs when the shielding electrode and the floating electrode have substantially the same potential. Preferably, both the floating and shielding electrodes will be at ground potential when the deposition is complete. The amount of powder to be deposited can therefore be controlled by controlling the bias potential, and it is unrelated to the duration of deposition, once the limit has been reached. Furthermore, the pattern of deposition is determined by the pattern of the floating electrodes, which creates a charge image.

Without being limited to a particular theory, the following mathematical formulas can be used to evaluate the amount of powder that can be held by the electrostatic chuck having a floating electrode, which is illustrated in the circuit diagram provided in FIG. 12. Referring to FIG. 12, C is the capacitance of the capacitor formed between the lower conductive layer $e_l$ and the floating electrode $e_f$. Cs is the stray capacitance of the capacitor formed between the floating electrode $e_f$ and the lower conductive layer $e_l$. C' is the capacitance of the capacitor formed between the floating electrode $e_f$ and the virtual electrode $e_v$, which is formed by the deposited charged powders. The potential of the floating electrode $e_f$ can only be some value between those of the shielding electrode $e_s$ and the lower conductive layer $e_l$, the shielding electrode $e_s$ being grounded in the circuit diagram shown in FIG. 12.

The maximum charge that the floating electrode can hold depends on the bias potential and the capacitor C according to the equation $Q_{max}$=CV. If the fringing field is ignored in order to calculate the maximum charge, the following equation applies:

$$Q_{max} = CV = \frac{\epsilon_0 \epsilon_r A}{d} V$$

where A is the surface area of the floating electrode and d is the thickness of the dielectric layer between the floating electrode and the shielding electrode.

Because $C_s$ is very small compared to C, the deposited charge Q' is approximately equal to Q. The mass M of the deposited powder will be as follows:

$$M = \frac{Q_{max}}{\mu} \cong \frac{\epsilon_0 \epsilon_r A}{d} \frac{m}{q} V$$

where μ is the charge over mass ratio of the charged powder. By way of example, if $\epsilon_r$=2, d=50 μm, the diameter of floating electrode=4 mm, μ=50 μC/g, and V=8 kV, M will be 1.2 mg. Thus, the maximum mass of powder expected to be deposited under these conditions will be 1.2 mg.

Since $C_s \ll C$, Q'=C'V'≈Q.

Therefore, the maximum amount of changed powder is provided by the following equation:

$$\frac{Q'}{\mu} \cong \frac{\epsilon_0 \epsilon_r A}{d} \frac{m}{q} V$$

In addition to providing electrostatic chucks, the present invention also provides methods of charge imaging or depositing particles onto selected areas of a substrate, the method including the use of an electrostatic chuck with floating electrodes in areas of the chuck that correspond to the selected areas of the substrate. Further, the present invention also provides for an object having selected areas in which particles are applied to the object via electrostatic means. In preferred embodiments, the particles comprise a pharmaceutically active ingredient. Preferably, the object is suitable for human consumption. In certain embodiments, the object comprises a pharmaceutical tablet, suppository dressing, bandage or a patch. Preferably, the amount of particles applied to the object are predetermined using a sensing electrode in the electrostatic chuck.

Advantages of the use of an electrostatic chuck for deposition of particles and for charge imaging include the ability to coat a substrate in a more accurate and more uniform manner, which is particularly important when the dosage of active ingredient is low, such as from about 1 μg to about 1 mg. Other low dosage ranges include for example, from about 1 μg to about 500 μg, and from about 10 μg to about 250 μg, and from about 20 μg to about 100 μg, such as about 25 μg. Further, the use of an electrostatic chuck for deposition of particles and for charge imaging provides the advantage, for example, of a mechanism for applying an active ingredient to a pharmaceutical carrier that may be immiscible or otherwise incompatible with the active ingredient.

In addition to providing electrostatic chucks with floating electrodes for charge imaging, the present invention provides chucks with sensing electrodes to sense the amount of charge deposited on a substrate. Furthermore, a single chuck can have both floating and sensing electrodes. In certain aspects of the present invention, the amount of charge that can be deposited on the chuck is limited to a finite number, and this limitation provides a mechanism for accurately determining the amount of powder deposited on the substrate held by the chuck. In another aspect, the present invention provides an electrostatic chuck having a sensing electrode for sensing the number of particles attracted to the chuck, particularly when the chuck is not self-limiting with respect to the amount of charged particles that can be deposited onto a substrate held by the chuck. This sensing electrode can be used, for example, to determine the amount of powder deposited onto a tablet, wherein the powder includes a pharmaceutically active ingredient. Thus, the present invention provides a more accurate and uniform way of dispensing a selected amount of pharmaceutically active ingredient on a substrate, especially when the active ingredient is present in small doses.

The sensing electrode preferably has two layers. The bottom layer is a lower conductive layer forming an electrode made of a metal, for example, such as aluminum. The top layer, which is exposed to the particles being deposited, is a dielectric layer, and is made of a material having a high dielectric strength, such as aluminum oxide. Additionally, for example, the sensing electrode can be made of a thin aluminized polypropylene sheet or a thin polyimide sheet with a copper backing. Without being limited to a particular theory, it is believed that the charged particles land on the dielectric layer and induce an equal and opposite charge on the conductive layer. Due to the presence of the dielectric layer, the possibility of charge neutralization is significantly lowered.

Figure 15A:
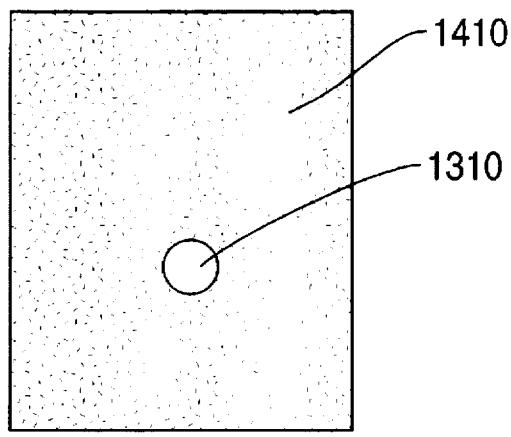
FIG. 15A is a top schematic view of a sensing electrode, with the location of the sensing electrode being inside the area of deposition.
Figure 15B:
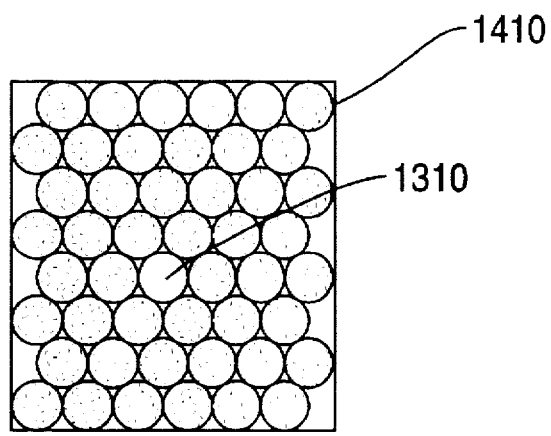
FIG. 15B is a top view of a schematic representation of a sensing electrode, with the location of the sensing electrode in the shape of a tablet, within the area of deposition.

Referring to FIG. 13, for example, the sensing electrode 1310 is constructed of a lower conductive layer 1320 and an upper dielectric layer 1330. As shown in FIG. 14, the sensing electrode 1310 can be placed, for example, in an area outside the substrate 1410 receiving the deposition of particles. In this figure, the sensing electrode 1310 is in the shape of a ring, and other shapes can also be used. The sensing electrode 1310 can also be placed, for example, within the area of the substrate 1410 receiving the deposition of particles as shown in FIG. 15A, when there is a single substrate 1410 receiving deposition. Alternatively, for example, when there are multiple substrates 1410, the sensing electrode 1310 can be placed within the area of deposition, preferably in the shape of one of the substrates 1410 receiving deposition, such as a tablet. Referring to FIG. 15B, for example, the shape of the sensing electrode 1310 mimics the shape of one of the substrates 1410.

The sensing electrode is preferably located in an area that provides for an amount of particles to be deposited on the sensing electrode in direct relation to the amount of deposition on the substrate. More than one sensing electrode can be used with a single substrate. For example, the presence of two sensing electrodes with deposition on a single substrate can be used to determine the relationship between the amount of deposition occurring on the substrate and in areas outside the substrate. The mass of the particles deposited onto the substrate(s) is determined once the charge of the sensing electrode is measured.

Figure 16:
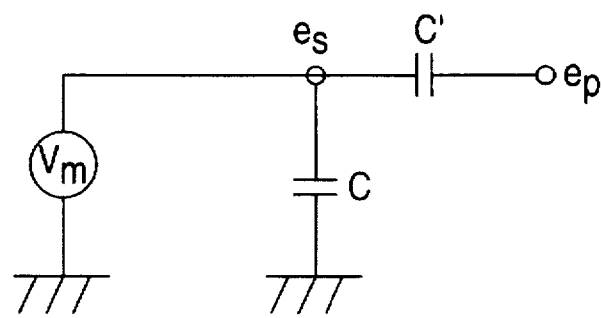
FIG. 16 is a circuit diagram of an electrostatic chuck with a sensing electrode.

To measure the amount of charge deposited, the sensing electrode is connected in series with a capacitor of known value. For example, a 1 nF capacitor will induce 1 volt when 1 nC of charge is collected. The other pole of the known capacitor is attached to ground, and the potential across the capacitor is measured. A circuit diagram to illustrate the set-up is shown in FIG. 16. Referring to FIG. 16, $V_m$ is a high impedance voltmeter or an electrometer, C is the capacitance of a capacitor of known value, such as 1 μF, C' is the capacitance of the capacitor formed between the sensing electrode $e_s$ and the deposited charge $e_p$ resulting from the deposition of charged particles.

Without being limited to a particular theory, the following mathematical formulas can be used to evaluate the measurement of deposited charges by the sensing electrode according to the above circuit diagram.

C' is the capacitor formed by the sensing electrode and the charged particles. C is a capacitor of known value. C has a zero initial charge. When charged particles land on the sensing electrode, they cause an equal amount of opposite charge to be induced on the electrode which will subsequently induce an equal amount of opposite charge on C. The overall effect results in an equal amount and equal sign of charge induced on C, which can be measured by an electrometer. Furthermore, the dominating electrical noise associated with an active power source is removed. The collected charge Q' is equal to C times V.

With this monitoring method using the sensing electrode, two parameters need to be predetermined to monitor the amount of actual deposition. These two parameters are the q/m (charge to mass) ratio of the charged powder and the relation factor k between the monitored charge Q' and the deposited charge Q on the deposition area of interest (i.e. k=Q/Q'). Hence, the deposited mass M is determined by the equation:

$$M = \frac{Q'}{k\frac{q}{m}}$$

The reliability of the sensing electrode requires that the variable k is substantially constant throughout the deposition.

The use of a sensing electrode is preferred over the use of an ammeter or voltmeter within the circuit since the sensing electrode provides the advantages, for example, of correcting for collection of charges from the ambient atmosphere and other leakage paths induced by the chuck.

Thus, in another aspect, the present invention provides a method of attracting a selected number of multiple particles to a substrate, comprising (a) providing an electrostatic chuck with a sensing electrode; (b) applying multiple electrostatically charged particles to the chuck; and (c) sensing the number of particles attracted to the chuck. Preferably, the particles are particles of a dry powder and the method is used to determine the amount of powder deposited on a substrate attracted to the chuck. The invention therefore provides a method of accurately determining the dosage in a pharmaceutical tablet.

Additionally, the invention provides a method of manufacturing a pharmaceutical composition comprising (a) providing a pharmaceutical substrate; and (b) electrostatically depositing particles on the substrate, the deposition preferably comprising the use of an electrostatic chuck.

Preferably, the electrostatic chuck comprises a floating electrode and the particles are substantially deposited on an area of the substrate corresponding to the floating electrode, and the electrostatic chuck preferably further comprises a sensing electrode for determining the amount of particles deposited on the substrate.

The invention additionally provides objects having selected areas in which particles are applied to the object via electrostatic means, such as charge imaging. The use of electrostatic means creates a more accurate deposition of particles in a selected image, thus providing for a manner of identification of such an object. The deposition also shows greater uniformity, and provides for less waste of particles.

In preferred embodiments, the particles comprise a pharmaceutically active ingredient, and the object is suitable for human consumption, and preferably comprises a pharmaceutical substrate such as a tablet, capsule or caplet. In other preferred embodiments, the object is a suppository or it is selected from the group consisting of a dressing, bandage and a patch. Preferably, the amount of particles applied to the object are predetermined using a sensing electrode in the electrostatic means. Additionally, in preferred embodiments, the particles are applied to the object using an acoustic dispenser described below.

In some of the embodiments of the present invention, a chuck is used to hold an object or multiple objects, optionally while particles are deposited onto the object. In other aspects of the invention, a chuck is used to position multiple particles, such as beads, optionally for transfer. These uses of the chucks require dispensing the particles on a substrate, which is optionally the chuck itself. Therefore, in another aspect of the present invention, an acoustic dispenser is provided in which particles are applied to a substrate using acoustic energy to propel the particles toward the substrate.

The use of an acoustic dispenser provides several advantages over the use of air, for example, to propel a powder for deposition. The advantages include, for example, the movement of particles in a directed manner rather than in a random manner, and a decrease in the amount of powder lost. Additionally, for example, the acoustic dispenser provides the ability to use an enclosed environment within the acoustic dispenser to deposit particles, which can be particularly advantageous when exposure to the particles is harmful to humans. Furthermore, for example, the acoustic dispenser can itself be used to tribocharge the particles, which provides for greater efficiency and is advantageous over corona charging, which can potentially alter the chemical nature of the particles.

In one aspect, the present invention provides an apparatus for depositing particles on a surface, comprising (a) a source of acoustic vibration; (b) a membrane for the application of acoustic vibration; and (c) a vessel for holding the particles. The acoustic dispensers of the invention can be used to create a powder cloud, for example, for application onto a substrate.

In another aspect, the present invention provides methods for depositing multiple particles on a surface, comprising (a) providing an apparatus having a membrane and a vessel for holding the particles, the particles being on the membrane; and (b) vibrating the membrane of the apparatus, thereby propelling the particles away from the membrane toward a surface for deposition. This method can be used, for example, to more accurately deposit a pharmaceutically active ingredient in the form of a powder onto a substrate such as a tablet, particularly when the active ingredient is present in a low dosage, such as about 25 µg.

In certain aspects of the invention, the particles dispensed by the acoustic dispenser are beads, which are preferably dispensed onto a chuck and can be positioned, for example, using the chucks described above.

In other preferred embodiments, the particles are in a micronized dry powder, which preferably comprises a pharmaceutically active ingredient. In one aspect, the acoustic dispensers of the present invention are used to deposit powder on a pharmaceutical substrate, such as a tablet. An electrostatic chuck can be used, for example, to hold the substrate while the powder is deposited onto the pharmaceutical substrate. Alternatively, for example, a vacuum chuck can be used to hold the substrate. The powder can be uniformly applied or applied using charge imaging, as described above. More than one type of powder can be deposited, including more than one pharmaceutically active ingredient.

In addition to powders containing pharmaceutical ingredients, the present acoustic dispenser invention can be used, for example, with dry paint particles, phosphor powder, and any other particles that can be triboelectrically charged.

Preferably, the powder is in micronized form and the particles are at least about 1 micron in diameter. Preferably, the powder is electrostatically charged before application to the acoustic dispenser, for example, through admixture with beads such as by mechanical shaking, preferably for about 30 minutes.

In preferred embodiments, the particles are electrostatically charged prior to or during dispensing the particles using the acoustic dispenser of the invention. Alternatively, for example, corona charging can be used when the particles would not be damaged by it, such as when the particles are beads. In certain aspects of the present invention, the vibration of the membrane of the acoustic dispenser can itself provide sufficient friction between particles to cause tribocharging, and the particles need not be charged prior to the use of the acoustic dispenser.

Preferably, a micronized powder will have particles ranging from about 4 to about 8 microns. A small particle such as this preferably has a carrier such as beads to charge the particle. A particle greater than about 50 microns can be charged directly without the use of beads.

In certain preferred embodiments, the particles comprise two types of particles, such as beads and a powder, and the acoustic dispenser further comprises a separating membrane for separating one type of particle from the other. Preferably, the separating membrane is located between the vessel and the surface for deposition, whereby one type of particle is separated from the other based on size differential prior to deposition on the surface. Thus, for example, the acoustic dispenser can be used to deposit a tribocharged powder that has been electrostatically charged through admixture with beads, the dispenser having a separating membrane that permits the powder to be deposited but causes the beads to remain within the dispenser. In certain preferred embodiments, this powder contains a pharmaceutically active ingredient, and is deposited onto a substrate, such as tablets, electrostatically held by a chuck.

Preferred materials for use in making an acoustic dispenser according to the present invention are as follows. The container for holding the objects is preferably made of glass or Teflon or another dielectric. Preferably, the membrane for acoustic vibration includes a dielectric layer on top of a conductive layer. For example, polyimide or Teflon can be used for the dielectric layer and copper can be used for the conductive layer. When made of Teflon, the dielectric layer is preferably about 15 mils in thickness. Preferably, the dielectric layer is on the side exposed to the objects to be vibrated. The separating membrane is preferably a #270 mesh (Newark Wire Cloth Co., Newark, N.J.) for particles from about 4 to about 6 microns in diameter and preferably a #200 mesh (Newark Wire Cloth Co., Newark, N.J.) for particles greater than about 6 microns.

Without being limited to a particular theory, it is preferable to apply a bias potential to the conductive layer on the membrane and the membrane for separating particles within the acoustic dispenser so that an electric field is generated whereby only particles with the correct charge are propelled from the dispenser. The conductive material onto which the powder will be applied also provides the opportunity for setting up an electric field with respect to the dispenser to further discriminate against incorrectly charged particles. For example, the membrane can be placed at 0 volts, the mesh at 500 volts and the tablet at −2000 volts. If a positively charged particle is selected to exit the dispenser, then a the membrane, which is the lowest layer, has a higher potential. The uppermost layer is the conductive substrate, such as a tablet, onto which the powder is deposited. If a negatively charged particle is selected, the lowest layer has a lower potential.

Figure 17:
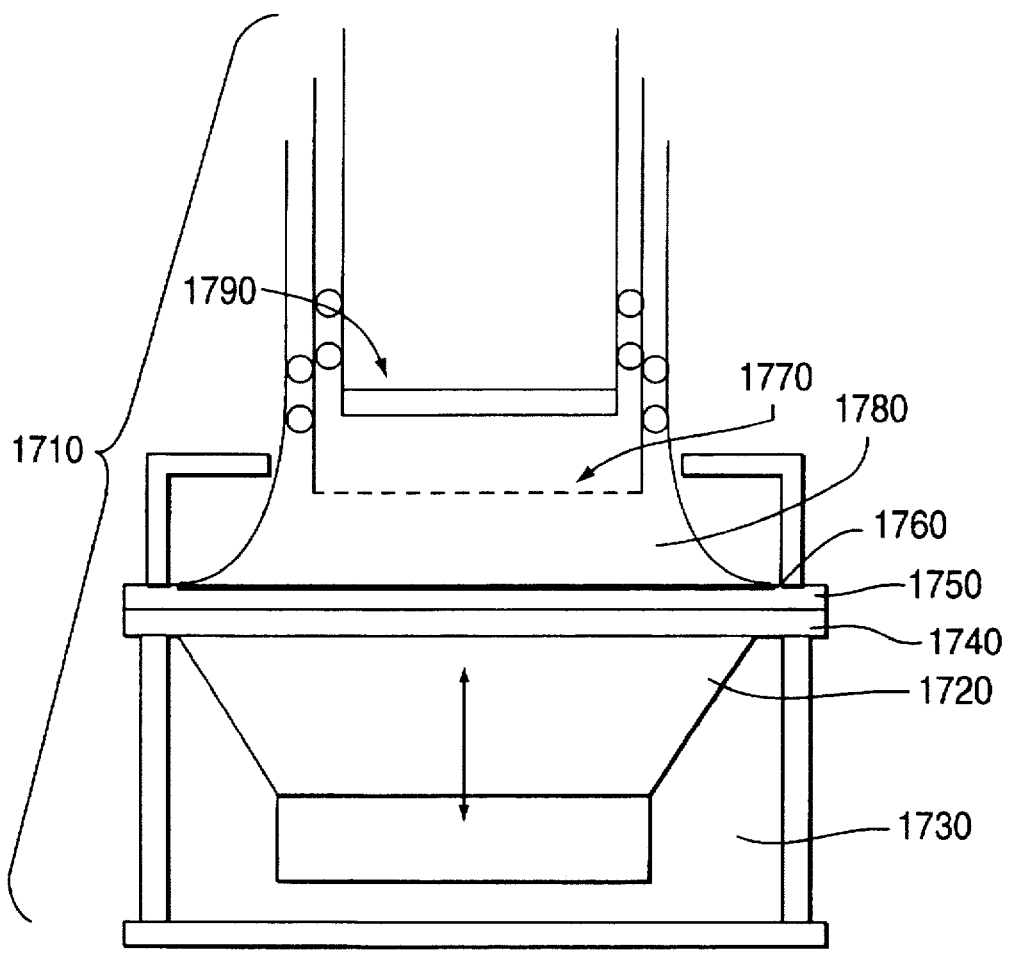
FIG. 17 is a cross-sectional schematic view of an acoustic dispenser according to the present invention.
Figure 18:
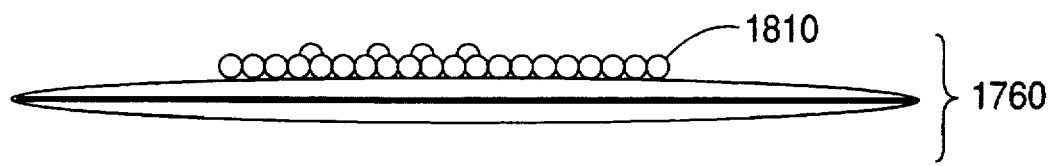
FIG. 18 is a cross-sectional schematic view of the membrane of an acoustic dispenser according to the present invention.

Referring to FIG. 17, for example, the acoustic dispenser 1710 has a speaker 1720 within a container 1730. On top of the speaker 1720 is a conductive layer 1740. On top of this layer 1740 is a dielectric layer 1750. On top of the dielectric layer 1750 is a membrane 1760, which is composed of a conductive layer and a dielectric layer, with the dielectric layer facing the outside and in contact with the particles (not shown) propelled by the membrane 1760. The membrane 1760 is further illustrated in FIG. 18, which illustrates the particles 1810 on top of the membrane 1760, which is shown as it is vibrating back and forth.

Referring again to FIG. 17, above the membrane 1760 for acoustic vibration is a separating membrane 1770, such as a mesh, for separating out particles having more than one size.

Figure 19:
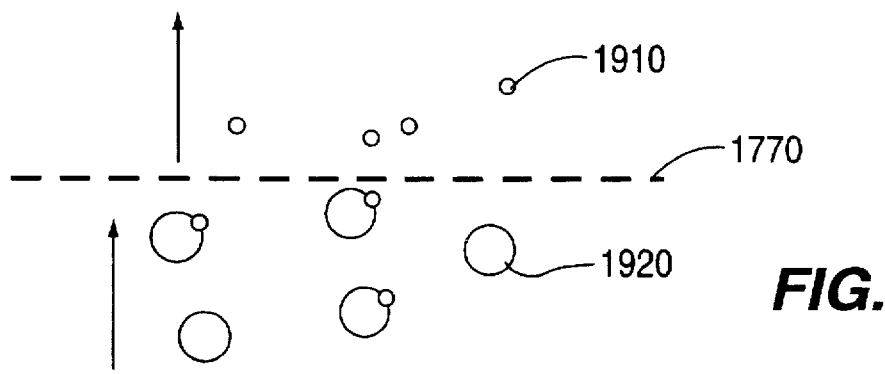
FIG. 19 is a cross-sectional schematic view of a mesh for separating objects within an acoustic dispenser of the present invention for dispensing objects less than about ten microns.

As illustrated in FIG. 19, the mesh 1770 allows only smaller particles 1910 to pass through, leaving larger particles 1920 behind it.

Referring once again to FIG. 17, the mesh 1770 is attached to a container 1780 for the particles (not shown), and the container 1780 has a design that enhances acoustic vibration, as shown. Above the mesh 1770 is a substrate 1790, for receiving the particles that are dispensed. The substrate 1790 can be, for example, a substrate attached to an electrostatic chuck.

Figure 21:
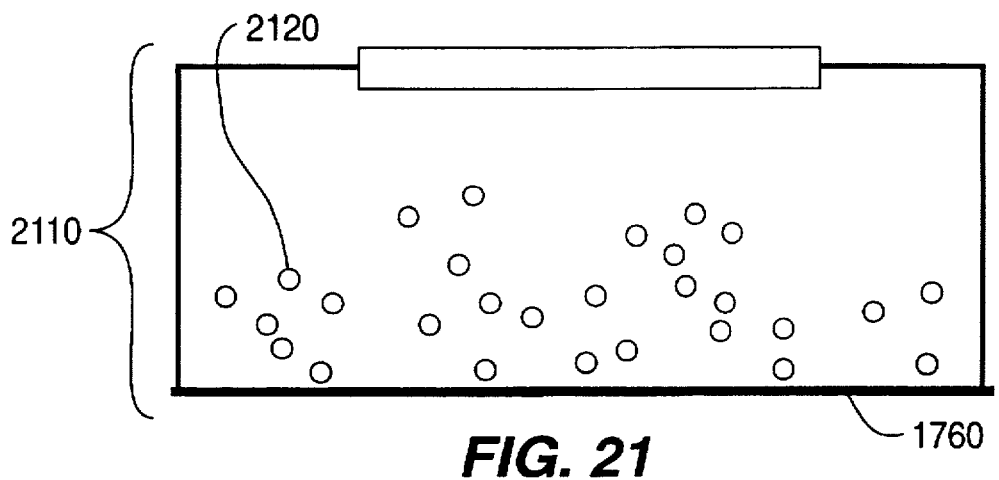
FIG. 21 is a cross-sectional view of a schematic representation of an acoustic dispenser according to the present invention.

Alternatively, for example, the structure of the acoustic dispenser is simplified in preferred embodiments, such as the diagram depicted in FIG. 21 which illustrates a container 2110 holding the particles 2120 which are propelled by the membrane 1760, the speaker (not depicted) being below the container 2110.

Figure 20:
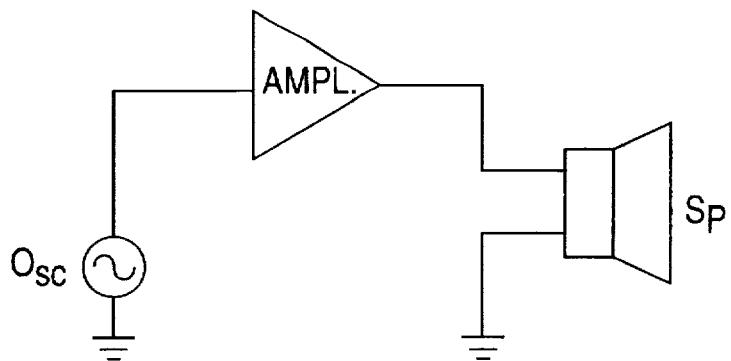
FIG. 20 is a circuit diagram of an acoustic dispenser according to the present invention.

A circuit diagram of the acoustic dispenser is illustrated in FIG. 20. Referring to FIG. 20, the oscillator $O_{sc}$ provides a single frequency oscillation for the audio amplifier $A_{mpl}$ to couple energy to the speaker $S_p$.

The oscillator $O_{sc}$ can be, for example, a single chip with tuning components.

Without being limited to a particular theory, the following mathematical formulas can be used to evaluate the force of propulsion of particles or other objects by the acoustic dispenser.

If the membrane is vibrating at an audible frequency, the motion at any point of the membrane can be described using the following equations:

$$z(t) = A\sin(\omega t)$$

$$v(t) = \frac{dz}{dt} = A\omega\cos(\omega t)$$

$$a(t) = \frac{d^2z}{dt^2} = -A\omega^2\sin(\omega t)$$

where A is the amplitude of vibration, z is the average displacement from any one position, v is the velocity, a is the acceleration and $\omega$ is the angular velocity of the wave.

For example, in a membrane, if A=2 mm and $\omega$=600; then the peak v=1.2 ms$^{-1}$ and the peak a=720 ms$^{-2}$. A particle at rest on the membrane will leave the membrane at a velocity smaller or equal to the peak v. At a leaving velocity of 1.2 ms$^{-1}$, the particle will reach a height of 7.35 cm before falling. If a mesh is placed in the path of the particle, the particle will hit the mesh and cause a momentum transfer. If the particle is a tribocharged bead with some attached powder, the momentum will be transferred to the powder. FIG. 19 schematically illustrates this action. As the bead 1920 and the powder 1910 are tribocharged, the powder 1910 escaping from the container will be charged. Inside a container, the amplitude of the vibration of the membrane can be maximized by operating the speaker at the resonant frequency of the container.

In another aspect of the present invention, when the acoustic dispenser is used with particles having an average diameter greater than about 10 microns and less than about 5 mm, the membrane for the application of acoustic vibration preferably comprises three layers. The top or uppermost layer is a conductive layer, which is preferably a mesh having multiple holes which are smaller than the average diameter of the particles, and more preferably smaller than the minimum diameter of the particles. Alternatively, for example, the mesh can be woven, with the spaces in between the rows and columns being smaller than the average diameter of the particles. The mesh can be made of a metal, for example, such as stainless steel, silver or copper. For example, a number 270 stainless steel mesh from Newark Wire Cloth Co. (Newark, N.J.) is preferably used with a particle having an average diameter of about 150 microns.

Preferably, the separating membrane is at least one inch from the vibrating membrane, and they are preferably from one to three inches apart.

Preferably, the mesh forming the membrane has a hole in the center without the conductive material, thereby forming a ring of conductive material in the membrane. For example, with a 5 inch membrane, preferably a circular area having a diameter of about 4 inches has the conductive material removed. Preferably the thickness of the Teflon is about 15 mils.

The second or middle layer is a dielectric layer. The dielectric layer can be made of any dielectric material with high dielectric strength, including, for example, polyimide and Teflon, and it is preferably ductile and provides for resistance to wear. The bottom layer is a lower conductive layer, preferably without holes extending through it, and can be made of a metal, for example, such as silver or copper.

Optionally, a fourth layer, for example, can be added to the membrane, such as a thin Teflon layer coated onto the wires of the mesh, and preferably is layered over both the wires and the gaps in the mesh. In addition to Teflon, other dielectrics can be used, the dielectric preferably having substantially the same triboelectric characteristics of the powder to be charged. A power source is connected to the membrane and preferably about 2000 volts is applied during operation.

For example, in order to propel a sufficient number of beads to an electrostatic chuck for attracting beads, the surface of the lower layer of the membrane is preferably grounded, the surface of the separating membrane is preferably at 3000 volts, the surface of the upper conductive layer of the chuck is preferably grounded and the lower electrode of the chuck is preferably −1500 volts.

The preferred number of beads used with the acoustic dispenser, using a bead with a diameter of 100 microns and a circular membrane with a diameter of about 12.5 cm, can be calculated as follows, the preferred number of beads "n" being in a close pack. $n=\pi D^2/\pi d^2=(D/d)^2=(12.5/100\times10^{-4})$, which is approximately equal to 1.6M. Assuming a density of 4 g/cc, the total mass (m) of the beads is calculated as follows. $m=n\times4/3\pi(d/2)^3\times\rho=1.6\times10^6\times\pi/3(100\times10^{-4})^3\times4$, approximately equal to 6.5 grams. Therefore, for 20 grams of bead, there are three layers of beads. Preferably, the amount of beads will be less than or equal to about 3 to about 4 layers.

Preferably, the beads used to charge the powder, the container to hold the powder-bead mixture, and the dielectric coating on the membrane are all made of the same material, such as Teflon, so that the charge on the powder will remain the same.

Preferably a magnetic shield is used if the speaker used to vibrate the membrane has a magnet or non-magnetic beads are preferably used.

Preferably the mesh of the acoustic dispenser is cleaned between uses.

Without being bound to a particular theory, it is believed that the larger particles to be deposited by the acoustic dispenser can carry more than one charge due to local charging in particular areas of the particle. It is believed that the mesh of the membrane in the acoustic dispenser generates multiple fringing electric fields on the edges of the holes of the mesh which polarizes the particles and enhances the tribocharging process. Additionally, the fringing fields will cause a particle having a charge opposite to the charge of the majority of particles to become trapped, and eventually become charged correctly. Thus, the construction of the three-layered membrane, using for example, a conductive mesh, enhances the tribocharging of the particles, and enhances the charge uniformity of the particles by orienting the charges on the particles in substantially one direction.

Figure 22A:
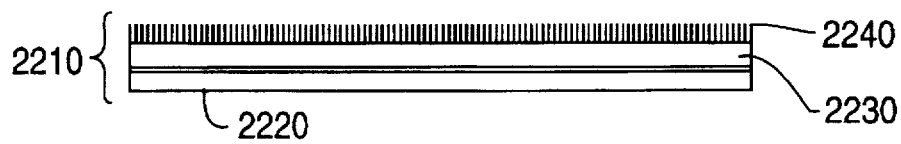
FIG. 22A is a cross-sectional view of a schematic representation of a mesh membrane of an acoustic dispenser according to the present invention, for dispensing objects greater than about ten microns in diameter.
Figure 22B:
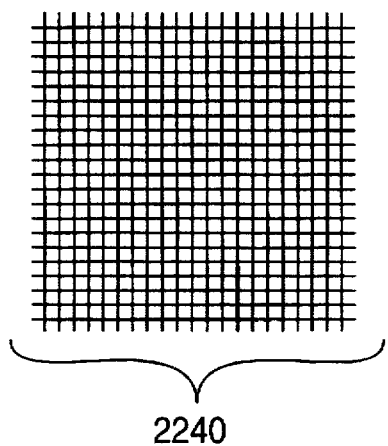
FIG. 22B is a top schematic view of a mesh membrane of an acoustic dispenser according to the present invention, for dispensing objects greater than about ten microns in diameter.
Figure 22C:
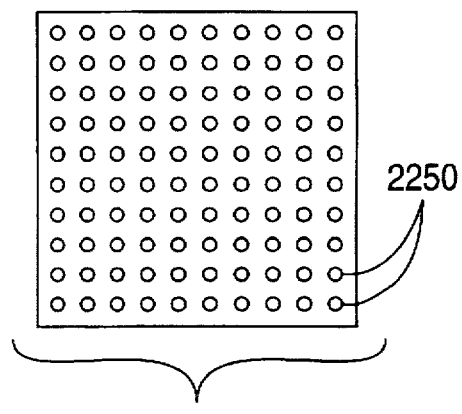
FIG. 22C is a top view schematic of a solid membrane with holes in it for an acoustic dispenser according to the present invention, for dispensing objects greater than about ten microns in diameter.

Referring to FIG. 22A, the membrane 2210 for acoustic vibration has a lower conductive layer 2220 with a dielectric layer 2230 on top of it. On top of the dielectric layer 2230 is a conductive layer 2240, which is illustrated as a mesh. A top view of the mesh 2240 is shown in FIG. 22B. An alternative construction is shown in FIG. 22C, in which the upper conductive layer 2240 has holes 2250 in it rather than being a wire mesh.

The vessel holding the objects is preferably made of a material that will not absorb the objects, such as glass or another triboelectrically compatible material that does not substantially charge the powder opposite in polarity to the charge on the powder due to the beads. In preferred embodiments, the vessel of the acoustic dispenser has a shape that enhances uniformity of acoustic vibration. See, for example, FIG. 17.

Preferably, the vibrating means in the acoustic dispenser is a speaker or multiple speakers, or more preferably, a piezoelectric device. The speaker can be any selected size, and is preferably about 20 watts. In other embodiments, the vibrating means is a mechanical vibrator, such as a piston, in which the frequency of vibrations lies within the audible (acoustic) range. Alternatively, for example, the vibrating means can use electrical energy, such as a motor with a low number of revolutions per minute. Preferably, the vibrating means is operated at the resonant frequency of the vessel holding the objects, which provides for the maximum amplitude of vibration of the membrane. Preferably, the acoustic frequency is stable during the deposition.

Preferably, the distance between the vibrating membrane and a membrane for separating different sizes of particles, such as a mesh, is at least about one-half inch to three inches. Preferably, the distance between the substrate for receiving the vibrating particles and the membrane for separating the particles is at least about 1 inch. The distance between the substrate and the vibrating membrane should be far enough to provide for uniformity of powder density, yet sufficiently near so that the kinetic energy needed to propel the objects is not dissipated.

The present invention is illustrated by the following non-limiting examples.

EXAMPLE 1
Vacuum Chuck That Can Be Used for Transporting Objects

A vacuum chuck is constructed as follows. Using a piece of Corning Pyrex 7740 glass, approximately 2 in. by 2 in. in area, and approximately 20 mils thick, via holes are drilled to match a microtiter plate onto which beads will be transferred. The microtiter plate selected is one having 10,000 wells. A mask is used to laser etch 100 vias at a time, in 10 rows by 10 columns, for a total of 10,000 vias, the layout of which corresponds to the array of the microtiter plate. The laser used is a Resonetics laser. The plate has a pitch of 965 microns, with a well size of 635 microns by 635 microns, and an overall area of 3.80 square inches. The diameter of the vias is about 50 microns, which is smaller than the bead diameter of about 150 microns.

A lower layer of Corning Pyrex 7740 glass is bonded to the upper layer having the vias. The lower layer has a cavity that extends to each of the vias. This cavity is chemically etched into the glass. The lower glass layer also has an opening for connection to a vacuum source. The two glass layers are bonded together.

To use the vacuum chuck, a vacuum wand is connected to the opening in the lower layer of the chuck. Beads are poured onto the via holes on the chuck. The beads are made of polyethylene glycol graft polystyrene (PEG-PS), obtained from PerSeptive and approximately 150 microns in diameter, on average. A vacuum is applied through the wand to the chuck, and beads are poured onto the chuck until there is one bead attached to each via.

To transport the beads to the 10,000 well microtiter plate, the chuck is inverted over the plate, the vias are aligned with the wells, and the vacuum is released.

EXAMPLE 2
Electrostatic Chuck with Conductive Vias That Can Be Used for Positioning and Transporting Objects An electrostatic chuck with conductive vias is constructed as follows. Using a piece of Corning Pyrex 7740 glass, approximately 2 in. by 2 in. in area, and approximately 20 mils thick, via holes are drilled to match a microtiter plate onto which beads will be transferred. A mask is used to laser etch 100 vias at a time, in 10 rows by 10 columns, for a total of 10,000 vias, the layout of which corresponds to the array of a microtiter plate having 10,000 wells described in Example 1 above. The laser used is a Resonetics laser. The diameter of the vias is about 50 microns, which is smaller than the bead diameter of about 150 microns. The via holes are then filled with a conductive ink composed of gold and glass particles in a liquid medium. The ink is forced through the via holes using a rubber diaphragm positioned on one side of the glass. The conductive ink is dried and fired.

Next, a dielectric material is layered on the top and bottom surfaces of the glass substrate. Conductive material is next deposited on one of the dielectric layers so that a conductive layer of approximately 500 nm in thickness is formed.

To use the electrostatic chuck, a voltage source is connected to the conductive layer. The beads are poured onto the via holes on the chuck. The beads are made of polyethylene glycol graft polystyrene (PEG-PS), obtained from PerSeptive and approximately 150 microns in diameter, on average. Voltage is applied to the chuck, and beads are poured onto the chuck until there is one bead attached to each via. Since the beads have a negative charge, a positive charge is applied to the chuck. Excess beads are removed from the chuck by inverting the chuck while the voltage is still applied.

To transport the beads to the 10,000 well microtiter plate, the chuck is inverted over the plate, the chuck is aligned with the plate so that the vias are aligned with the wells, and the application of voltage is stopped or reversed.

EXAMPLE 3
Electrostatic Chuck That Can Be Used for Transporting Objects

An electrostatic chuck is constructed as follows. A lower conductive layer is formed of a copper layer on polyimide, which is a middle layer of the chuck and is a dielectric material. The conductive layer is about 10 microns thick and the dielectric layer is about 25 microns thick. An upper conductive layer is placed on top of the polyimide layer, using conductive tape. The upper conductive layer is made of copper (Minnesota Mining and Manufacturing radio frequency shielding product), and is approximately 1 mil in thickness. Prior to applying the upper conductive layer, a pin is used to form openings in the conductive tape. The diameter of the openings is about 280 microns, which is smaller than the bead diameter of about 500 microns.

To use the electrostatic chuck, a voltage source is connected to the upper conductive layer, which is the layer having openings in it. The beads are dispensed onto the chuck using an acoustic dispenser according to Example 9. The beads are made of polystyrene obtained from Polysciences Inc. (Warrington, Pa.) and approximately 500 microns in diameter, on average. Voltage is applied to the chuck so that the chuck has a potential of −1500 volts compared to the 3000 volt potential of the acoustic dispenser, and beads are dispensed onto the chuck until there is one bead attached to each opening. Since the beads have a positive charge, a negative charge is applied to the chuck.

To transport the beads to a microtiter plate, the chuck is inverted over the plate, the openings are aligned with the wells, and the application of voltage is stopped or reversed.

EXAMPLE 4
Electrostatic Chuck with an Upper Conductive Layer Having Two Interdigitated Electrodes An electrostatic chuck with an upper conductive layer having two interdigitated electrodes was fabricated as follows. A glass substrate was used, the substrate having an ITO (indium tin oxide) interdigitated electrode, forming an upper conductive layer less than about 25 microns thick. On top of the upper conductive layer was a thin polystyrene layer using Scotch brand tape, having about 1 mil thickness.

In one test, 1000 volts was applied across the electrodes and a tablet weighing about 65 mg and having a diameter of about 5.6 mm was held to the chuck. When 1400 volts were applied, the tablet was repelled from the chuck, possibly due to a surge resulting in a discharge due to a repulsive force.

In a second test, a tablet was placed on top of the tape and 500 V D.C. was applied to the electrodes. The chuck was turned upside down and the tablet was held in place by the chuck.

In a third test, three tablets were applied to the chuck using 500 V and the voltage was decreased until all three fell off the chuck. The first tablet fell off at 300 V, the second tablet fell off at 200 V, and the third tablet fell off at 100 V. The test results showed that the holding force is proportional to $V^2$.

In another test, six hundred volts was applied to one of the two interdigitated electrodes of the chuck, and the other electrode was grounded. One tablet was placed on the polystyrene side of the chuck, and the tablet remained on the chuck after turning the chuck upside down and subjecting the tablet to the force of gravity.

The chuck was also tested for depositing powder on a tablet while held by the chuck. Using air propulsion to deposit a positively charged steroid in a 3% suspension of beads, it was determined that at least about 47 μg was deposited.

EXAMPLE 5
Electrostatic Chuck with a Single Electrode in the Upper Conductive Layer An electrostatic chuck having a single electrode in the upper conductive layer was configured as follows. The bottom of the chuck was a lower conductive layer made of aluminum layered onto a dielectric layer made of polyimide laminated onto copper (Good Fellows, Berwyn, Pa.). The thickness of the polyimide layer was about 2 mils. Three copper wires on top of the polyimide formed the upper conductive layer, and functioned as an electrode. The thickness of the copper layer was about 4 mils. The distance between the copper wires was about 5.6 mm. Eighty-six tablets were used, each having a diameter of about 5.6 mm and each weighing about 65 mg, and being made of about 95% cellulose and about 3% lactose, each with a thickness of about 2 mm. The tablets were adhered to the chuck for approximately five minutes, using 1500 volts applied between the upper and lower conductive layers.

A steroid drug powder was applied to the tablets held by the chuck described above as follows. A mixture of 3% drug with Kynar coated steel beads (Vertex Image Products, Yukom, Pa.) having a diameter of about 100 microns was stored in a Teflon bottle. 585.0 mg of drug powder, in a combination of drug and beads weighing 20.6354 g, was deposited on the tablets for about 6 minutes, using the acoustic dispenser described in Example 8 below at a frequency of 87 Hz, which was determined to be the optimum frequency for the dispenser. The mesh of the acoustic dispenser for separating drug powder from beads was placed at a distance of 0.5 to 1.0 inches from the tablets receiving the powder.

EXAMPLE 6
Electrostatic Chuck with Floating Electrodes

An electrostatic chuck with floating electrodes having the following configuration was tested. The lower conductive layer was made of copper tape and was about 4 mils in thickness. The next layer was a dielectric layer made of Scotch brand polystyrene tape and about 1 mil in thickness. On top of the dielectric layer was an upper conductive layer made of a standard multipurpose through hole wire wrapped board (Radioshack) and about 0.0625 inch thick, forming an electrode, with a gap between a shielding electrode and a floating electrode, which are electrically connected. The floating electrode was round, and about 2.1 mm in diameter. The shielding electrode was round, and about 2.5 mm in diameter. The gap between the shielding and the floating electrode was about 200 microns. A substrate was placed on the upper conductive layer, the substrate being a dielectric layer made of Scotch brand polystyrene tape and about 1 mil in thickness.

To use the chuck, about −1800 volts were applied to the upper conductive layer. Next, steroid drug particles were applied to the chuck using the dispenser described in Example 8.

Figure 23A:
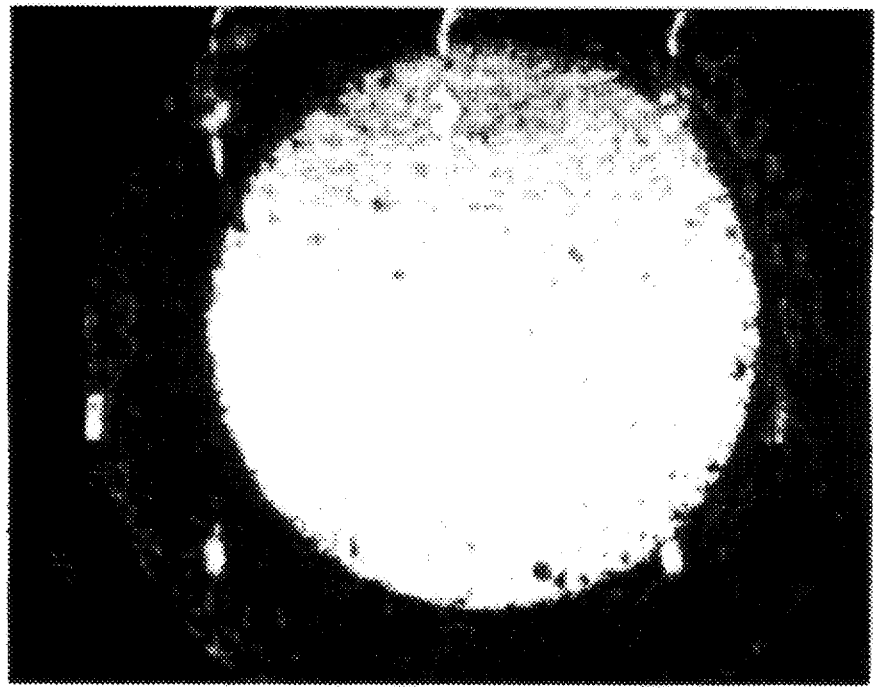
FIG. 23A is a photograph of a top view of a floating electrode after powder deposition, in a chuck without the lower conductive layer, with the printed circuit board attached. The photograph was taken at about 50×magnification; therefore, the line adjacent to the photograph represents a length of about 0.5 mm therein.
Figure 23B:
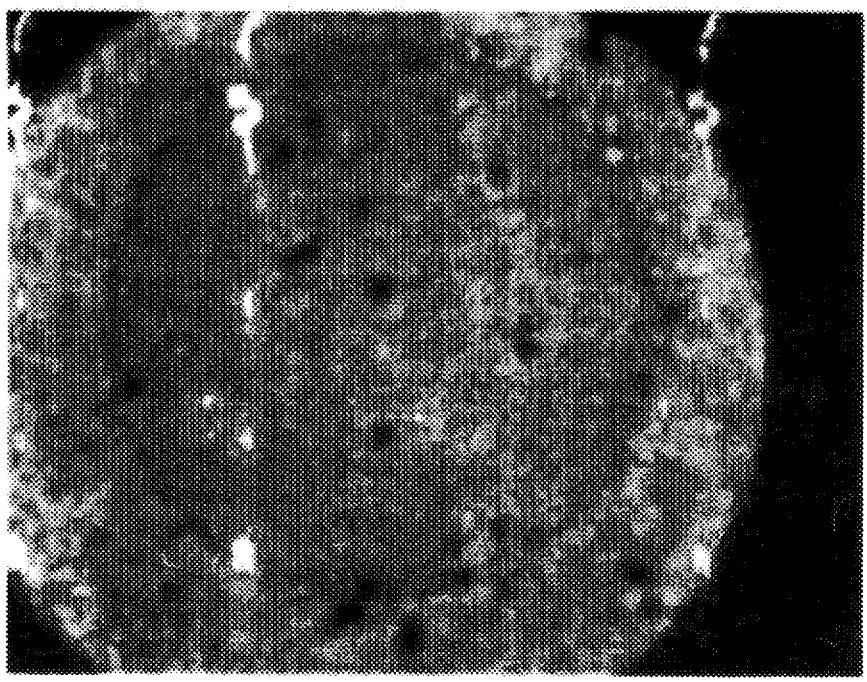
FIG. 23B is a photograph of a top view of a floating electrode after powder deposition, in a chuck with the lower conductive layer, with the printed circuit board attached. The photograph was taken at about 50×magnification; therefore, the line adjacent to the photograph represents a length of about 0.5 mm therein.
Figure 24A:
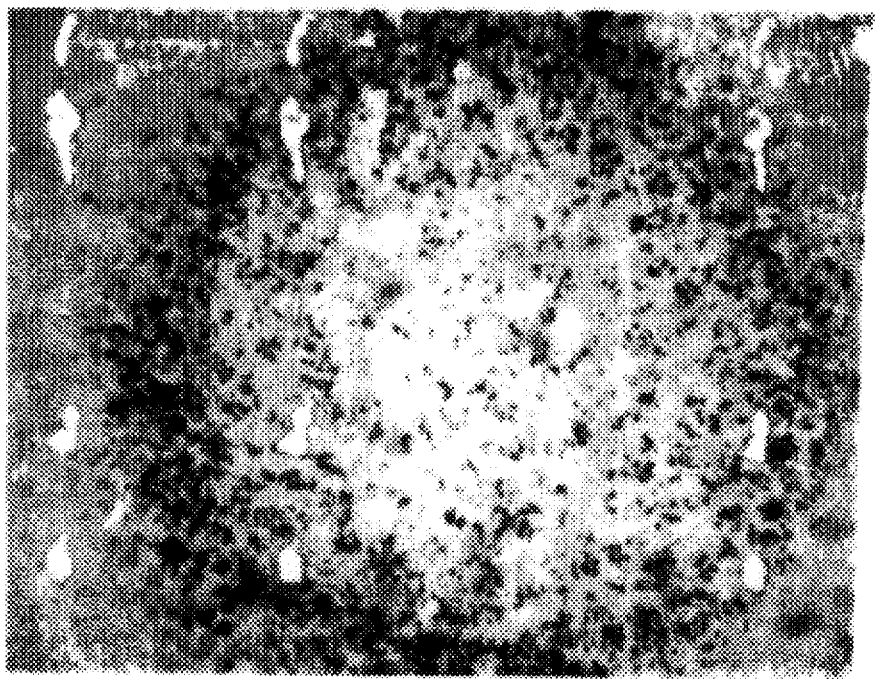
FIG. 24A is a photograph of a top view of a floating electrode after powder deposition, in a chuck without the lower conductive layer, with the printed circuit board removed. The photograph was taken at about 50×magnification; therefore, the line adjacent to the photograph represents a length of about 0.5 mm therein.
Figure 24B:
FIG. 24B is a photograph of a top view of a floating electrode after powder deposition, in a chuck with the lower conductive layer, with the printed circuit board removed. The photograph was taken at about 50×magnification; therefore, the line adjacent to the photograph represents a length of about 0.5 mm therein.

FIGS. 23A, 23B, 24A and 24B show the deposition of the powder on a floating electrode using a bias potential of −1800 volts with the chuck described above. The lower conductive layer, which is a printed circuit board, shows the control of the alignment of the powder during deposition. In FIGS. 23A and 24A, the lower conductive layer was omitted whereas in FIGS. 23B and 24B, it was present. FIG. 23A shows that, in the absence of the lower conductive layer, the charged particles accumulate at the edges of the floating electrode. FIGS. 23B and 24B, in contrast, show that in the presence of the lower conductive layer, the charged particles are uniformly spread throughout the floating electrode. The greatest quantity of powder deposited was found in the conditions present in FIG. 24B, in the presence of the lower conductive layer.

EXAMPLE 7
Electrostatic Chuck with Sensing Electrode

An electrostatic chuck with a sensing electrode is constructed as follows. The sensing electrode consists of a lower conductive layer made of aluminum and having on top of it a dielectric layer made of aluminum oxide. A sensing electrode is placed on the electrostatic chuck so that it is outside the recipient substrate that is subject to deposition. The sensing electrode is used to indirectly determine the amount of deposition of charged particles by measuring the change in charge before and after deposition.

Another electrostatic chuck is constructed with a sensing electrode placed on the chuck in an area within the recipient substrate, thereby causing both the sensing electrode and the recipient substrate to be subject to deposition. In this case, the sensing electrode is used to directly determine the amount of deposition of charged particles by measuring the change in charge before and after deposition.

A third electrostatic chuck is constructed with two sensing electrodes, one placed within the recipient substrate, and the other placed outside the recipient substrate. In this case, the sensing electrode within the recipient substrate is used to directly determine the amount of deposition of charged particles by measuring the change in charge before and after deposition, and is also used to calibrate the measurement of deposition by the sensing electrode outside the area of deposition.

A sensing electrode in a ring configuration was fabricated using anodized aluminum oxide (aluminum as the conductive layer forming the electrode and the oxide layer as the dielectric). 15 g of beads were used and were shaken together with a micronized steroid drug powder (cortisone, Aldrich Chemical Co., Milwaukee Wis.) for about 30 minutes. Two concentrations of powder were used, one having 450 mg of powder per 15 g beads (3% mixture) and one having 900 mg of powder for 15 g beads (6% mixture). 1800 volts were applied to the electrostatic chuck. Acoustic energy was used to propel the powder according to Example 8, using either 1400 (corresponding to about 12 Watts), 1600 or 1800. The change in charge during deposition was measured by recording the voltage on the electrometer every 30 seconds for the first two minutes and every minute thereafter until 30 minutes total had passed. The amount of powder deposited on a pre-weighed amount of aluminum foil was also measured.

Figure 25A:
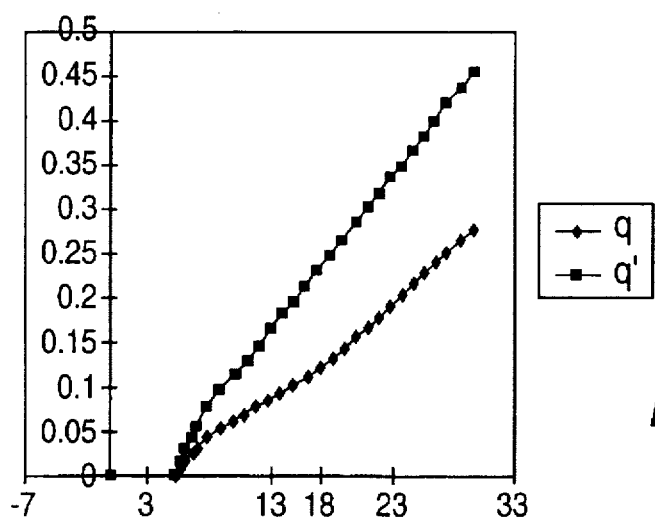
FIGS. 25A–C are graphical representations of the detection of powder deposited using a sensing electrode with an electrostatic chuck of the present invention. The x axis represents the time in minutes and the y axis represents the charge in microcoulombs. dq/dt represents the deposition rate.
Figure 25B:
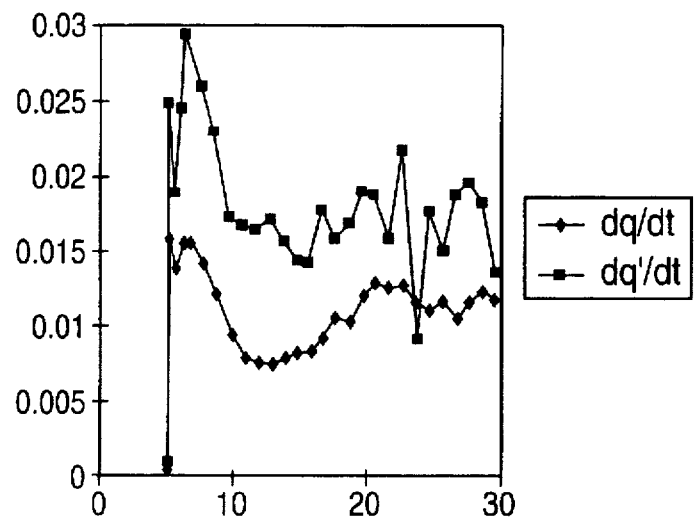
Figure 25C:
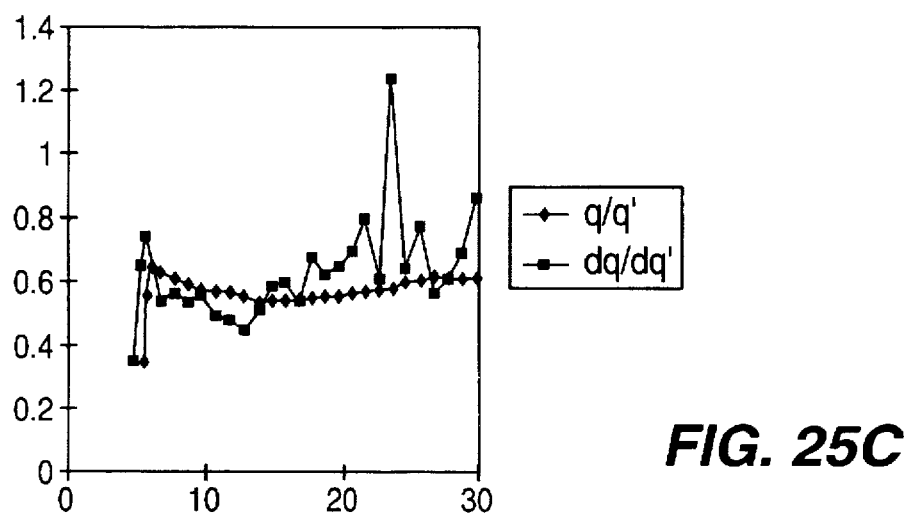

Multiple tests were undertaken by performing deposition on aluminum foil, the time for complete deposition taking about five minutes. Tests showed that with steady state deposition, k varies up to 4% in either direction. k is the ratio between the monitored charge Q' and the deposited charge Q and is actually a function of all operational parameters of the chuck and acoustic dispenser; therefore, k is determined experimentally. A k inconsistency in excess of 10% is accompanied by a change of dispenser characteristic. The data obtained in tests of the sensing electrode is provided in Tables VI and VII below, and FIGS. 25A–C, which provide a graphical representation of the experimental data using a sensing electrode in the guard ring configuration.

TABLE VI

Experimental Data of Sensing Ring Testing

| Time | Q | Q' | AudioSe | Time | q | q' | Time | dq/dt | dq'/dt | Time | q/q' | dq/dq' | q/q' analysis | |
|---|---|---|---|---|---|---|---|---|---|---|---|---|---|---|
| 0 | 0.00021 | 0.00115 | 900 | 0 | 0 | 0 | 5 | 0.000372 | 0.001102 | 5 | | 0.337568 | average after 18 minutes | 0.58499 |
| 5 | 0.00207 | 0.00666 | 1600 | 5 | 0.00186 | 0.00551 | 5.5 | 0.01576 | 0.02488 | 5.5 | 0.337568 | 0.633441 | Std deviation | 0.020353 |
| 5.5 | 0.00995 | 0.0191 | 1600 | 5.5 | 0.00974 | 0.01795 | 6 | 0.0138 | 0.01886 | 6 | 0.542618 | 0.731707 | Relative deviation | 0.034792 |
| 6 | 0.01685 | 0.02853 | 1600 | 6 | 0.01664 | 0.02738 | 6.5 | 0.01546 | 0.02458 | 6.5 | 0.607743 | 0.62897 | average after 7 minutes | 0.569577 |
| 6.5 | 0.02458 | 0.04082 | 1600 | 6.5 | 0.02437 | 0.03967 | 7 | 0.0156 | 0.02956 | 7 | 0.614318 | 0.52774 | Std deviation | 0.026827 |
| 7 | 0.03238 | 0.0556 | 1600 | 7 | 0.03217 | 0.05445 | 8 | 0.01429 | 0.02603 | 8 | 0.590817 | 0.548982 | Relative deviation | 0.0471 |
| 8 | 0.04667 | 0.08163 | 1600 | 8 | 0.04646 | 0.08048 | 9 | 0.01218 | 0.02307 | 9 | 0.577286 | 0.527958 | average after 5 minutes | 0.561399 |
| 9 | 0.05885 | 0.1047 | 1600 | 9 | 0.05864 | 0.10355 | 10 | 0.00951 | 0.0173 | 10 | 0.566296 | 0.549711 | Std deviation | 0.052168 |
| 10 | 0.06836 | 0.122 | 1600 | 10 | 0.06815 | 0.12085 | 11 | 0.00804 | 0.01675 | 11 | 0.563922 | 0.48 | Relative deviation | 0.092925 |
| 11 | 0.0764 | 0.13875 | 1600 | 11 | 0.07619 | 0.1376 | 12 | 0.00768 | 0.0165 | 12 | 0.553706 | 0.465455 | | |
| 12 | 0.08408 | 0.15525 | 1600 | 12 | 0.08387 | 0.1541 | 13 | 0.0076 | 0.01725 | 13 | 0.544257 | 0.44058 | | |
| 13 | 0.09168 | 0.1725 | 1600 | 13 | 0.09147 | 0.17135 | 14 | 0.00804 | 0.0157 | 14 | 0.53382 | 0.512102 | average over 25 minutes | 25 |
| 14 | 0.09972 | 0.1882 | 1600 | 14 | 0.09951 | 0.18705 | 15 | 0.00841 | 0.0146 | 15 | 0.531997 | 0.576027 | Deposition rate (mg/min) | 1.0056 |
| 15 | 0.10813 | 0.2028 | 1600 | 15 | 0.10792 | 0.20165 | 16 | 0.00845 | 0.0144 | 16 | 0.535185 | 0.586806 | Dep. rate (µg/min/mm2) | 0.580515 |
| 16 | 0.11658 | 0.2172 | 1600 | 16 | 0.11637 | 0.21605 | 17 | 0.00946 | 0.0178 | 17 | 0.538625 | 0.531461 | Dep. rate (µg/min/tablet) | 14.40048 |
| 17 | 0.12604 | 0.235 | 1600 | 17 | 0.12583 | 0.23385 | 18 | 0.01075 | 0.016 | 18 | 0.53808 | 0.671875 | Time for 35 µg (low dose) | 2.430474 |
| 18 | 0.13679 | 0.251 | 1600 | 18 | 0.13658 | 0.24985 | 19 | 0.01048 | 0.017 | 19 | 0.546648 | 0.616471 | Time for 250 µg (high dose) | 17.36053 |
| 19 | 0.14727 | 0.268 | 1600 | 19 | 0.14706 | 0.26685 | 20 | 0.01216 | 0.0191 | 20 | 0.551096 | 0.636649 | g/m (µC/g) | 11.79282 |

TABLE VI-continued

Experimental Data of Sensing Ring Testing

| Time | Q | Q' | AudioSe | Time | q | q' | Time | dq/dt | dq'/dt | Time | q/q' | dq/dq' | q/q' analysis | |
|---|---|---|---|---|---|---|---|---|---|---|---|---|---|---|
| 20 | 0.15943 | 0.2871 | 1600 | 20 | 0.15992 | 0.28595 | 21 | 0.01305 | 0.0189 | 21 | 0.556811 | 0.690475 | | |
| 21 | 0.17248 | 0.306 | 1600 | 21 | 0.17227 | 0.30485 | 22 | 0.0127 | 0.016 | 22 | 0.565098 | 0.79375 | Average last 5 minutes | 5 |
| 22 | 0.18518 | 0.322 | 1600 | 22 | 0.18497 | 0.32085 | 23 | 0.01293 | 0.0218 | 23 | 0.5765 | 0.593119 | Deposition rate (mg/min) | 1.054461 |
| 23 | 0.19811 | 0.3438 | 1600 | 23 | 0.1979 | 0.34265 | 24 | 0.01179 | 0.0095 | 24 | 0.577557 | 1.241053 | Dep. rate (μg/min/mm2) | 0.608722 |
| 24 | 0.2099 | 0.3533 | 1600 | 24 | 0.20969 | 0.35215 | 25 | 0.0113 | 0.0177 | 25 | 0.595456 | 0.638418 | Dep. rate (μg/min/tablet) | 15.10019 |
| 25 | 0.2212 | 0.371 | 1600 | 25 | 0.22099 | 0.36985 | 26 | 0.0118 | 0.0153 | 26 | 0.597513 | 0.771242 | Time for 35 μg (low dose) | 2.317852 |
| 26 | 0.233 | 0.3863 | 1600 | 26 | 0.23279 | 0.38515 | 27 | 0.0107 | 0.019 | 27 | 0.604414 | 0.563158 | Time for 250 μg (high dose) | 16.55609 |
| 27 | 0.2437 | 0.4053 | 1600 | 27 | 0.24349 | 0.40415 | 28 | 0.0118 | 0.0197 | 28 | 0.602474 | 0.598985 | | |
| 28 | 0.2555 | 0.425 | 1600 | 28 | 0.25529 | 0.42385 | 29 | 0.0125 | 0.0183 | 29 | 0.602312 | 0.68306 | | |
| 29 | 0.268 | 0.4433 | 1600 | 29 | 0.26779 | 0.44215 | 30 | 0.0119 | 0.0138 | 30 | 0.605654 | 0.862319 | | |
| 30 | 0.2799 | 0.4571 | 1600 | 30 | 0.27969 | 0.45595 | | | | | | | | |

TABLE VII dg/dg' analysis

| | |
|---|---|
| average after 18 minutes | 0.733839 |
| Std deviation | 0.192065 |
| Relative deviation | 0.261727 |
| average after 7 minutes | 0.629475 |
| Std deviation | 0.16644 |
| Relative deviation | 0.264411 |
| average after 5 minutes | 0.633389 |
| Std deviation | 0.157774 |
| Relative deviation | 0.249094 |
| Foil mass before deposition | 160.86 |
| Foil mass after deposition | 186 |
| Mass gain | 25.14 |
| Length (in) | 1.79 |
| Width (in) | 1.5 |
| Area (in2) | 2.685 |
| Area (mm2) | 1732.255 |
| Tablet diameter (mm) | 5.62 |
| Tablet area (mm2) | 24.80639 |
| Capacitor value (μF) | 1.06 |

EXAMPLE 8

Acoustic Dispenser for Particles Less Than About Ten Microns in Diameter

An acoustic dispenser for deposition of particles less than about ten microns in diameter was constructed as follows. A speaker was mounted onto an aluminum plate supported by four pieces of ¾ inch aluminum posts, and an aluminum plate was placed on top of the speaker. A teflon plate was placed on top of the aluminum plate. A membrane made of a mil thick Teflon sheet on a conductive layer was placed on top of the teflon plate. A Corning Pyrex glass cylinder was placed above the membrane and sealed with o-rings. Within the glass cylinder, a mesh was placed above the membrane to separate particles of different sizes, the mesh being a #270 mesh from Newark Wire Cloth Co. (Newark, N.J.).

The opening of the glass cylinder permits the placement of a recipient substrate on an electrostatic chuck.

The speaker was activated, and a suspension of 15 g beads and 450 mg powder was used, resulting in the particles of the powder being dispersed in a cloud through the mesh onto the tablet substrate.

EXAMPLE 9

Acoustic Dispenser for Particles More Than About Ten Microns in Diameter

The configuration of an acoustic dispenser for the deposition of particles, such as beads, with a diameter greater than about ten microns was as follows. A Radioshack speaker, catalog number 40-1354A, was placed below an acrylic box with a hinged lid. Inside the acrylic box was a membrane. Suspended above the membrane was an electrostatic chuck for receiving the beads.

The membrane was fabricated using polyimide on copper substrate and a #270 stainless steel mesh from Newark Wire Cloth Co. (Newark, N.J.). Polystyrene beads (Polyscience) with a diameter of 500 μm were used for testing.

The dispenser was activated by applying the beads to the membrane and activating the speaker. The beads were applied to a one mil thick Scotch brand polystyrene tape placed on a metal plate to measure the charge-to-mass ratio of the bead.

Using a bias potential of +1300 V applied to the mesh, 30 nC was collected at a floating plate. 156.6 mg of beads were collected on the floating plate. A q/m (charge to mass ratio) value of 240 nC/g was calculated. At a bias of −1300V at the mesh, 1 nC was collected and a few beads were collected. These results indicate that the mesh served to positively tribocharge the beads. Further, the use of a teflon layer on top of the mesh may enhance the performance of the acoustic dispenser at −1300 V.

We claim:

1. An apparatus for positioning multiple objects in a selected configuration, each object having a thickness less than about three millimeters, comprising an electrostatic chuck comprising:
a conductive layer;

a first insulating layer; and a substrate layer, wherein the substrate layer comprises a multitude of conductive vias extending from a top of the substrate layer to a bottom of the substrate; wherein the electrostatic chuck is activated by applying a bias voltage to the conductive layer, and wherein points on the outer surface nearest the vias define attraction points for positioning the objects.

2. The apparatus of claim 1, wherein the substrate layer is glass.

3. The apparatus of claim 1, wherein the first insulating layer is less than 50 mm thick.

4. The apparatus of claim 1, wherein the first insulating layer insulates at least about 2000 V.

5. The apparatus of claim 1, further comprising:

a second insulating layer adjacent to the substrate layer on the side of the substrate layer opposite the first insulating layer.

6. The apparatus of claim 1, wherein the vias have diameter less than that of the objects that are to be positioned.

7. The apparatus of claim 1, wherein the conductive layer is divided into separate sectors and further comprising electrical connectors and switches allowing voltage to be selectively applied to each sector, a subset of the sectors or all of the sectors so that the objects are positioned at the sector(s) to which voltage has been applied.

8. The apparatus of claim 1, comprising the following sequentially arranged:

the conductive layer;

the substrate layer; and a second conductive layer, wherein the second conductive has openings and the objects electrostatically adhere to the apparatus at the openings.

9. The apparatus of claim 8, wherein the openings are smaller in diameter than the objects the apparatus is adapted to position.

10. The apparatus of claim 8, wherein the dielectric layer insulates at least about 500 V.

* * * * *